US012667279B1

(12) United States Patent
Meckenzie et al.

(10) Patent No.: US 12,667,279 B1
(45) Date of Patent: Jun. 30, 2026

(54) SYSTEMS AND METHODS FOR CLOUD MEDIATED EXERTION CHALLENGES

(71) Applicant: Ares Tech. Inc., Middletown, DE (US)

(72) Inventors: Shalom Meckenzie, Savyon (IL); Tal Soffer, Ramat Gan (IL); Rebecca Shultz, San Carlos, CA (US); Amir Levanon, Sunnyvale, CA (US)

(73) Assignee: AMP FIT ISRAEL LTD, Tel Aviv (IL)

( * ) Notice: Subject to any disclaimer, the term of this patent is extended or adjusted under 35 U.S.C. 154(b) by 349 days.

(21) Appl. No.: 18/333,465

(22) Filed: Jun. 12, 2023

Related U.S. Application Data

(60) Provisional application No. 63/496,605, filed on Apr. 17, 2023, provisional application No. 63/433,463, filed on Dec. 18, 2022, provisional application No. 63/351,406, filed on Jun. 12, 2022.

(51) Int. Cl.
*A61B 5/11* (2006.01)

(52) U.S. Cl.
CPC ........... *A61B 5/1118* (2013.01); *A61B 5/1116* (2013.01)

(58) Field of Classification Search
CPC . A61B 5/1118; A61B 5/1116; A63B 24/0075; A63B 71/0622; A63B 71/0616; A63B 24/0062; A63B 23/1227; A63B 23/0405; A63B 22/0023; A63B 22/025; A63B 2225/20; A63B 2071/0694; A63B 2071/0675; A63B 2071/0658; A63B 2071/065; A63B 2071/0625; A63B 2024/0081
See application file for complete search history.

(56) References Cited

U.S. PATENT DOCUMENTS

| | | | | |
|---|---|---|---|---|
| 32,345 | A * | 5/1861 | Bartholow | F42B 5/18 102/431 |
| 219,059 | A * | 9/1879 | Anders | G10K 1/063 379/418 |
| 5,104,120 | A * | 4/1992 | Watterson | A63B 22/025 482/7 |
| 5,947,868 | A * | 9/1999 | Dugan | A63F 13/211 482/4 |
| 6,902,513 | B1 * | 6/2005 | McClure | A63B 24/0006 482/4 |

(Continued)

*Primary Examiner* — Garrett K Atkinson

(74) *Attorney, Agent, or Firm* — FINNEGAN, HENDERSON, FARABOW, GARRETT & DUNNER L.L.P.

(57) ABSTRACT

User-initiated and cloud mediated exertion challenge operations are disclosed. A sensor captures first sensor data reflecting a first subject performing a first exertion, the sensor data reflecting at least one parameter associated with the first exertion. The first sensor data is converted into a challenge, and the challenge is transmitted to a selected second subject. An electronic acceptance of the challenge is received from the second subject, and a second sensor captures second sensor data reflecting the second subject performing a second exertion. An electronic comparison of the first sensor data and the second sensor data confirms that the second exertion complies with the at least one parameter, and then metrics of the first sensor data and the second sensor data are compared to determine a challenge dominator. A report is output to the first subject and the second subject identifying the challenge dominator.

23 Claims, 27 Drawing Sheets

(56) References Cited

U.S. PATENT DOCUMENTS

| | | | | |
|---|---|---|---|---|
| 7,746,997 B2* | 6/2010 | Brunson | G09B 5/06 | 434/323 |
| 7,927,253 B2* | 4/2011 | Vincent | A63B 24/0087 | 482/8 |
| 8,001,472 B2* | 8/2011 | Gilley | A63B 22/02 | 715/834 |
| 8,376,910 B2* | 2/2013 | Cheung | G06F 3/011 | 482/901 |
| 8,545,369 B2* | 10/2013 | Cheung | A63B 24/0084 | 482/8 |
| 8,579,767 B2* | 11/2013 | Ellis | G16H 20/10 | 482/901 |
| 9,174,085 B2* | 11/2015 | Foley | A63B 24/0075 | |
| 9,623,285 B1* | 4/2017 | Ruiz | G01C 9/00 | |
| 9,636,567 B2* | 5/2017 | Brammer | A63B 71/0622 | |
| 10,009,644 B2* | 6/2018 | Aimone | G06F 3/015 | |
| 11,040,247 B2* | 6/2021 | Casalini | A63B 71/0622 | |
| 12,290,721 B2* | 5/2025 | Meckenzie | A63B 21/072 | |
| 2003/0093248 A1* | 5/2003 | Vock | A42B 3/0433 | 702/188 |
| 2003/0199366 A1* | 10/2003 | Anderson | A63B 22/0242 | 482/54 |
| 2004/0102931 A1* | 5/2004 | Ellis | A61B 5/0833 | 702/188 |
| 2006/0136173 A1* | 6/2006 | Case | G01C 22/006 | 702/182 |
| 2007/0032345 A1* | 2/2007 | Padmanabhan | A63B 24/00 | 482/8 |
| 2007/0116207 A1* | 5/2007 | Brunson | G09B 7/02 | 379/90.01 |
| 2007/0219059 A1* | 9/2007 | Schwartz | A61B 5/329 | 482/8 |
| 2008/0076637 A1* | 3/2008 | Gilley | G06Q 30/0201 | 482/9 |
| 2008/0086318 A1* | 4/2008 | Gilley | G16H 10/20 | 705/319 |
| 2009/0098524 A1* | 4/2009 | Walton | G09B 5/14 | 434/350 |
| 2009/0233771 A1* | 9/2009 | Quatrochi | G16H 20/30 | 434/247 |
| 2010/0048358 A1* | 2/2010 | Tchao | A63B 24/0084 | 482/8 |
| 2011/0082008 A1* | 4/2011 | Cheung | A63B 24/0062 | 482/8 |
| 2013/0125025 A1* | 5/2013 | Cheung | G06F 3/048 | 715/753 |
| 2013/0237374 A1* | 9/2013 | Ashby | A63B 71/0054 | 482/4 |
| 2014/0172135 A1* | 6/2014 | Eisner | G06F 17/40 | 700/91 |
| 2014/0223462 A1* | 8/2014 | Aimone | G16Z 99/00 | 725/10 |
| 2015/0182800 A1* | 7/2015 | Watterson | A63B 22/02 | 482/4 |
| 2017/0186444 A1* | 6/2017 | Lu | G10L 15/08 | |
| 2017/0281079 A1* | 10/2017 | Nachman | H04L 67/306 | |
| 2018/0126248 A1* | 5/2018 | Dion | A63B 1/00 | |
| 2018/0126249 A1* | 5/2018 | Consiglio | A63B 24/0062 | |
| 2018/0140903 A1* | 5/2018 | Poure | A63B 71/0622 | |
| 2019/0005373 A1 | 1/2019 | Nims et al. | | |
| 2019/0126099 A1 | 5/2019 | Hoang | | |
| 2020/0015736 A1* | 1/2020 | Alhathal | A61B 5/11 | |
| 2021/0252336 A1* | 8/2021 | Dornan | A63B 24/0062 | |
| 2021/0322828 A1* | 10/2021 | Gherscovici | A61B 5/6824 | |
| 2022/0023739 A1* | 1/2022 | DeGooyer | A63B 24/0006 | |
| 2022/0223254 A1* | 7/2022 | Foley | A63B 24/0084 | |
| 2023/0089962 A1 | 3/2023 | Shavit | | |
| 2024/0316409 A1* | 9/2024 | Christiano | A63B 24/0062 | |
| 2024/0359058 A1* | 10/2024 | Cohen | A63B 21/0058 | |
| 2024/0359059 A1* | 10/2024 | Cohen | A63B 21/072 | |
| 2025/0001262 A1* | 1/2025 | Boyd-Surka | A63B 22/0605 | |

* cited by examiner

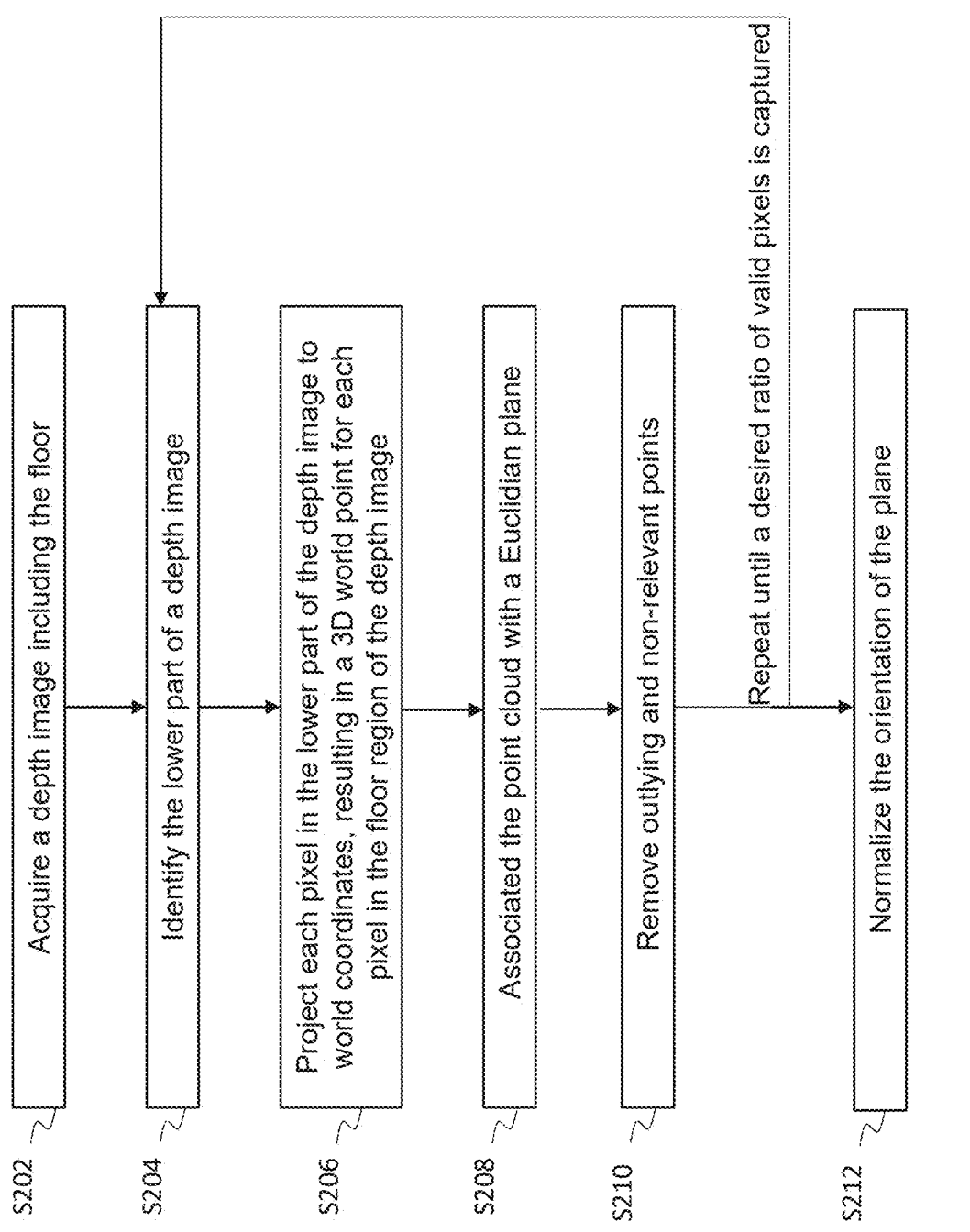

S202 Acquire a depth image including the floor

S204 Identify the lower part of a depth image

S206 Project each pixel in the lower part of the depth image to world coordinates, resulting in a 3D world point for each pixel in the floor region of the depth image

S208 Associated the point cloud with a Euclidian plane

S210 Remove outlying and non-relevant points

Repeat until a desired ratio of valid pixels is captured

S212 Normalize the orientation of the plane

*FIG. 2*

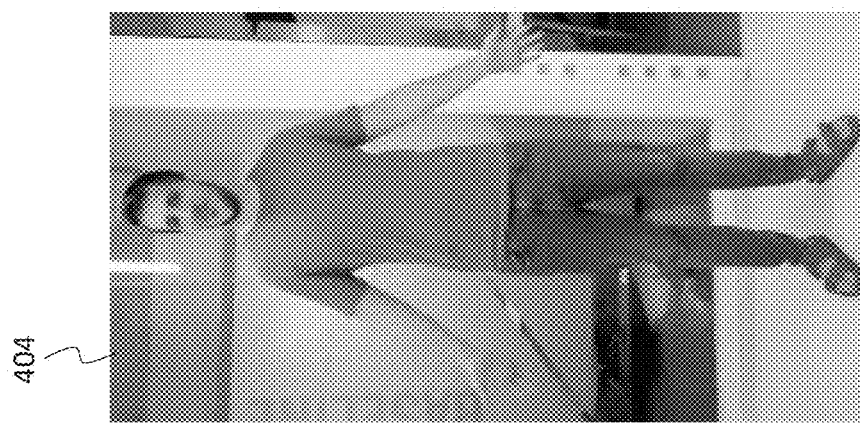
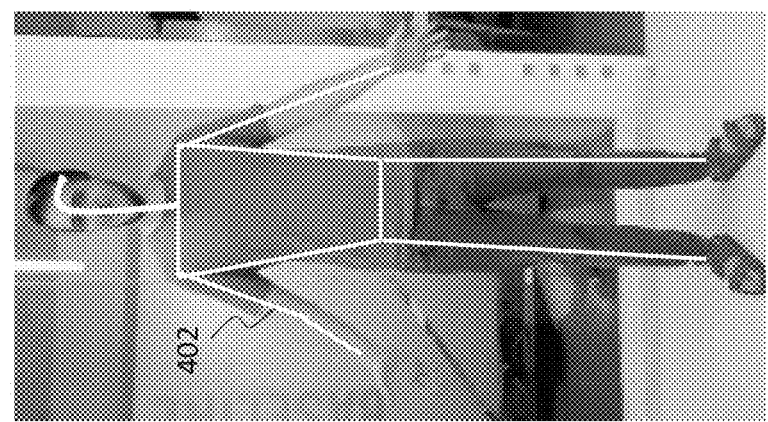
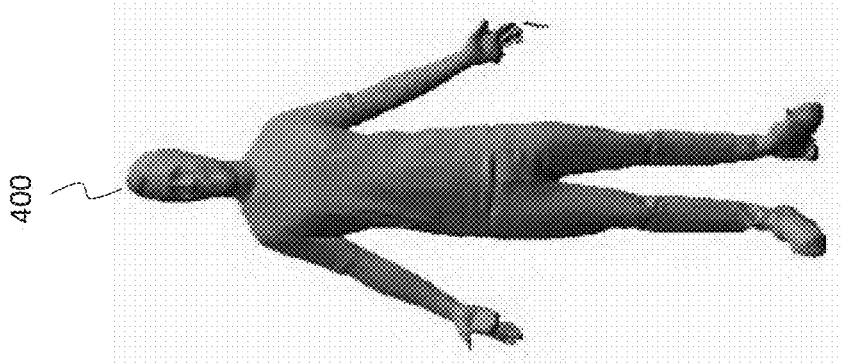
*FIG. 4*

CHALLENGE

How many jumps can you do?

🕒 20 SECONDS

⬍ ABOVE 15 CM

Total Players: 19                Scoreboard                Total Jumps: 365

| RANK | SCORE | PLAYER | RANK | SCORE | PLAYER |
|---|---|---|---|---|---|
| 1 | 41 | TaniaTania | 11 | 18 | Sapir M. |
| 2 | 40 | Sagie | 12 | 10 | Moroosh |
| 3 | 37 | Sapir M. | 13 | 1 | Me e. |
| 4 | 31 | Sapir n. | 14 | 1 | f f. |
| 5 | 30 | Its M. | 15 | 0 | Fabio F. |
| 6 | 26 | Hello | 16 | 0 | Its Me M. |
| 7 | 25 | Moshe s. | 17 | 0 | Sagi |
| 8 | 23 | Its Me M. | 18 | 0 | Sapir 333 3. |
| 9 | 23 | x O. | 19 | 0 | Its Me M. |
| 10 | 23 | Fabio The King | | | |

*FIG. 6K*

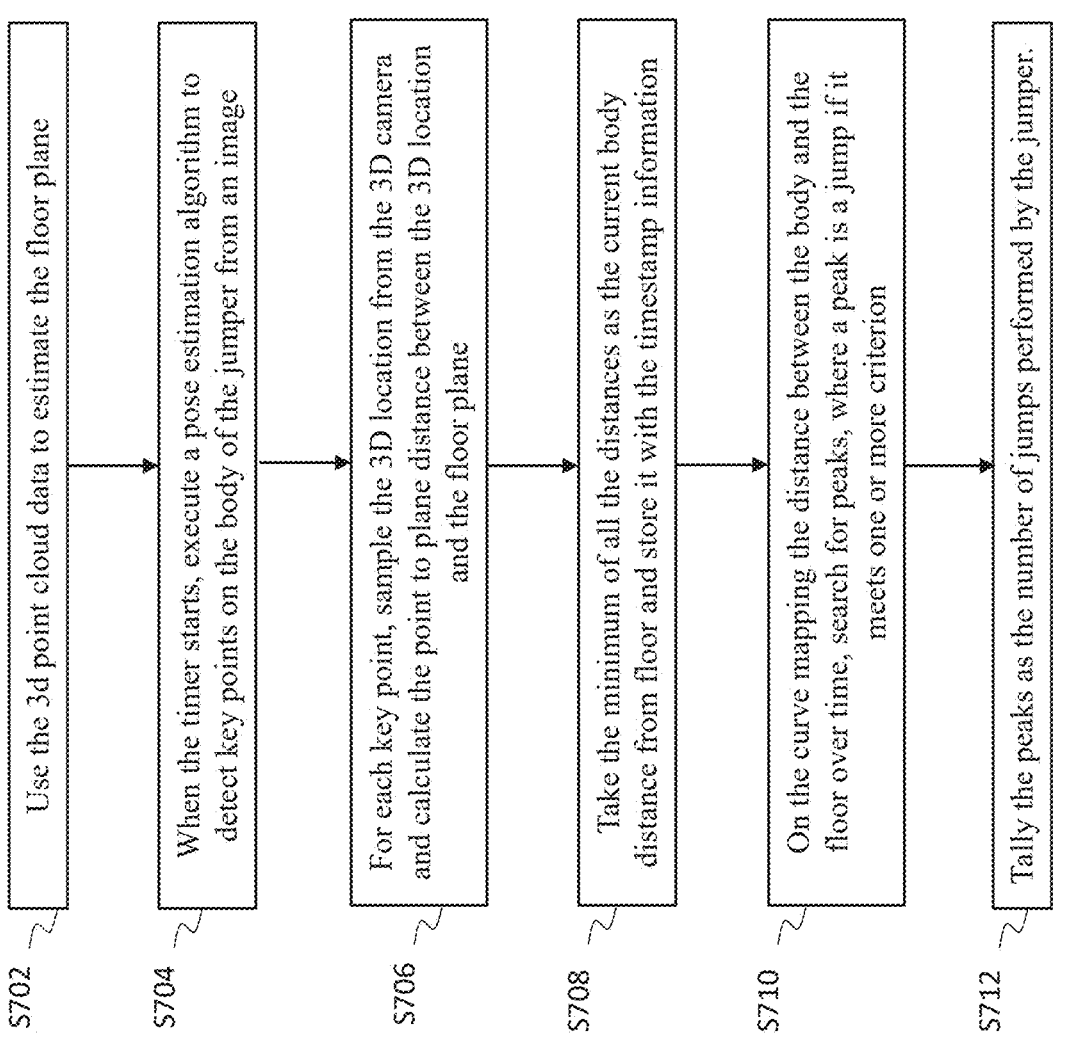

S702  Use the 3d point cloud data to estimate the floor plane

S704  When the timer starts, execute a pose estimation algorithm to detect key points on the body of the jumper from an image S706  For each key point, sample the 3D location from the 3D camera and calculate the point to plane distance between the 3D location and the floor plane S708  Take the minimum of all the distances as the current body distance from floor and store it with the timestamp information S710  On the curve mapping the distance between the body and the floor over time, search for peaks, where a peak is a jump if it meets one or more criterion S712  Tally the peaks as the number of jumps performed by the jumper.

FIG. 7

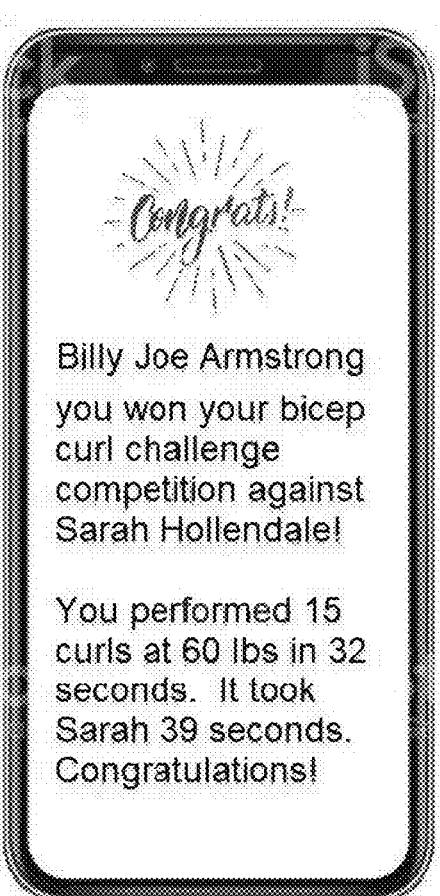
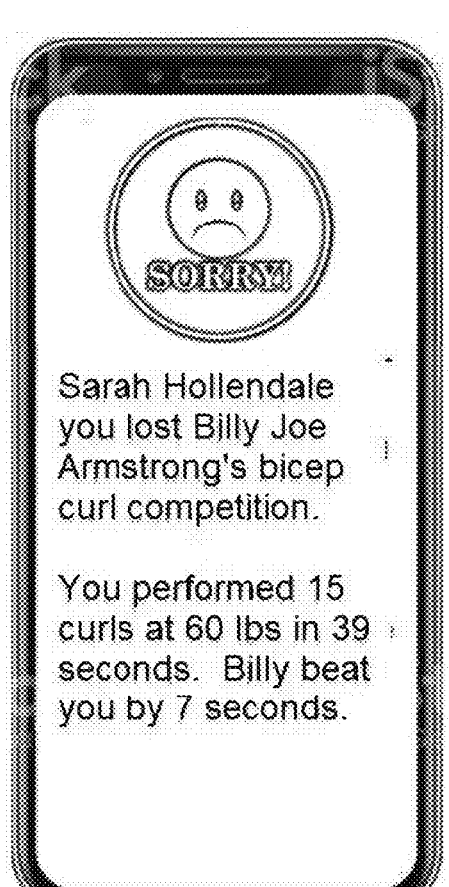
FIG. 11

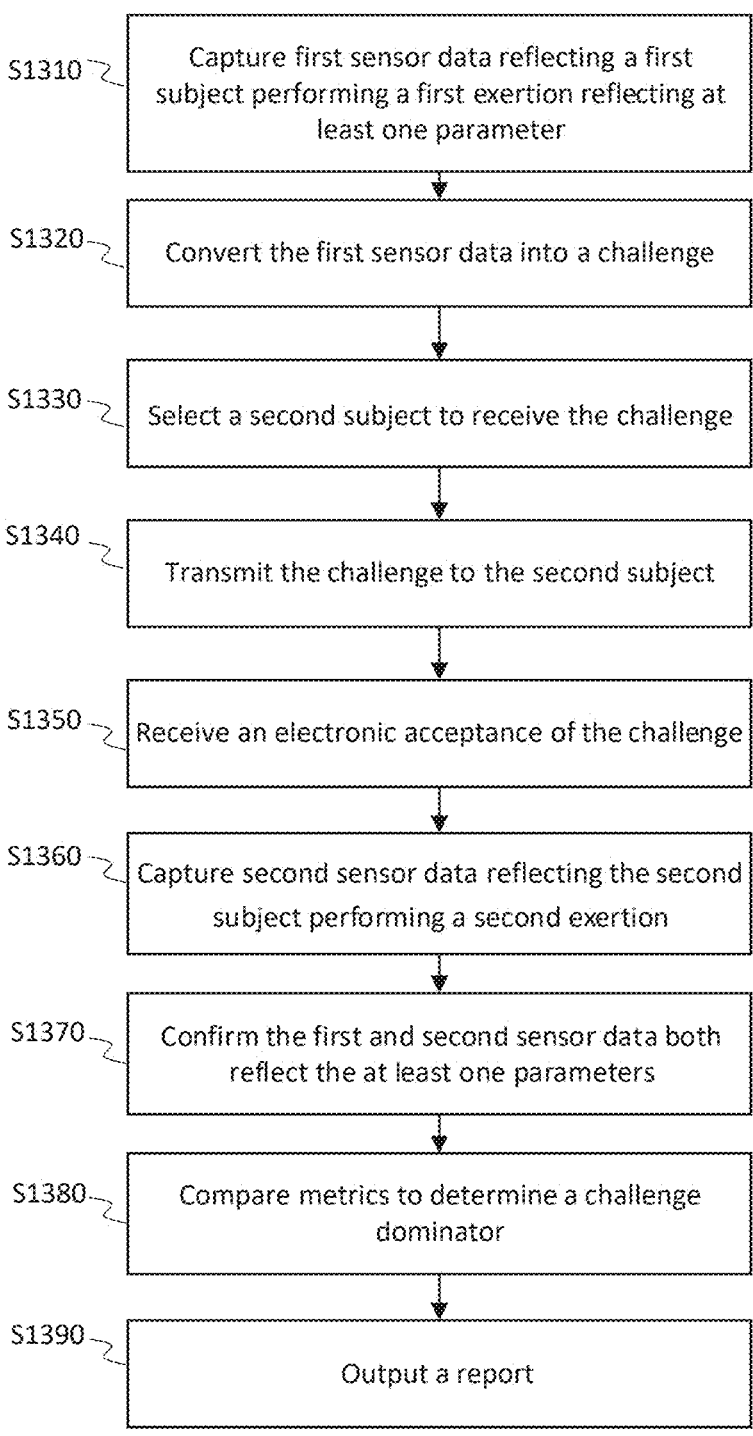

S1310 — Capture first sensor data reflecting a first subject performing a first exertion reflecting at least one parameter S1320 — Convert the first sensor data into a challenge S1330 — Select a second subject to receive the challenge S1340 — Transmit the challenge to the second subject S1350 — Receive an electronic acceptance of the challenge S1360 — Capture second sensor data reflecting the second subject performing a second exertion S1370 — Confirm the first and second sensor data both reflect the at least one parameters S1380 — Compare metrics to determine a challenge dominator S1390 — Output a report

*FIG. 13*

SYSTEMS AND METHODS FOR CLOUD MEDIATED EXERTION CHALLENGES

CROSS REFERENCE TO RELATED APPLICATIONS

This application claims the benefit of priority of U.S. Provisional Patent Application No. 63/351,406, filed on Jun. 12, 2022; U.S. Provisional Patent Application No. 63/433, 463, filed on Dec. 18, 2022; and U.S. Provisional Patent Application No. 63/496,605, filed on Apr. 17, 2023, all of which are incorporated herein by reference in their entirety.

TECHNICAL FIELD

This disclosure relates to systems, methods, and computer readable media associated with electronic exercise machines and exertion challenges.

BACKGROUND

Exercise and resistance training promotes the building and strengthening of muscles and bone tissue, and burns fat. While electronic exercise machines may facilitate resistance training, such machines tend to be large, bulky, heavy, and tedious to use. Some electronic exercise systems may be programmed with predefined routines, that while providing some degree of convenience, may offer only limited adjustment or customization capability to accommodate individual users, and may lack abilities to interact with other users. Consequently, some electronic exercise systems may be awkward, difficult, or tedious to use and may discourage users from engaging in exercise routines beneficial to their health. Therefore, there is a need for unconventional innovative streamlined technologies that occupy less space, offer a convenient interface to allow adjusting and customizing exercise routines, and enhance user interaction to suit individual needs.

SUMMARY

Embodiments consistent with the present disclosure provide systems, methods, and devices for electronic exercise machines.

Some embodiments involve systems, methods, and computer readable media for asynchronous user-initiated and cloud mediated exertion challenge operations. Such embodiments may involve capturing, via at least a first sensor, first sensor data reflecting a first subject performing a first exertion, the first sensor data reflecting at least one parameter associated with the first exertion. An input may be received to convert the first sensor data into a challenge, and a selection of a second subject for receipt of the challenge may be received, causing transmission of the challenge to the second subject. An electronic acceptance of the challenge may be received from the second subject, and a second sensor may capture second sensor data reflecting the second subject performing a second exertion. Operations may further include confirming via electronic comparison of the first sensor data and the second sensor data that the second exertion complies with the at least one parameter, and when the electronic comparison confirms that the second exertion complies with the at least one parameter of the first exertion, comparing metrics of the first sensor data and the second sensor data to determine a challenge dominator. Operations may further include outputting a report to the first subject and the second subject identifying the challenge dominator.

Consistent with other disclosed embodiments, non-transitory computer-readable storage media may store program instructions, which are executed by at least one processing device and perform any of the methods described herein.

The foregoing general description and the following detailed description are exemplary and explanatory only and are not restrictive of the claims.

BRIEF DESCRIPTION OF FIGURES

FIG. 2 is a block diagram of an exemplary method for assessing the surface plane (e.g., for a floor, platform, stage, table top, etc.) consistent with some disclosed embodiments.

FIG. 4 is illustrations of an exemplary 3D model and an exemplary skeletal map of key points of a jumper.

FIGS. 6A-6L are illustrations of exemplary user interface screens associated with an implementation of a jumping challenge, consistent with some disclosed embodiments.

FIG. 7 is a flowchart illustrating an exemplary method for a CV engine facilitating a jumping competition, consistent with some disclosed embodiments.

FIG. 11 illustrates two examples of a common report consistent with some disclosed embodiments.

FIG. 13 is a flowchart illustrating a method for asynchronous user initiated and cloud mediated exertion challenge operations consistent with some disclosed embodiments.

DETAILED DESCRIPTION

Figure 1A:
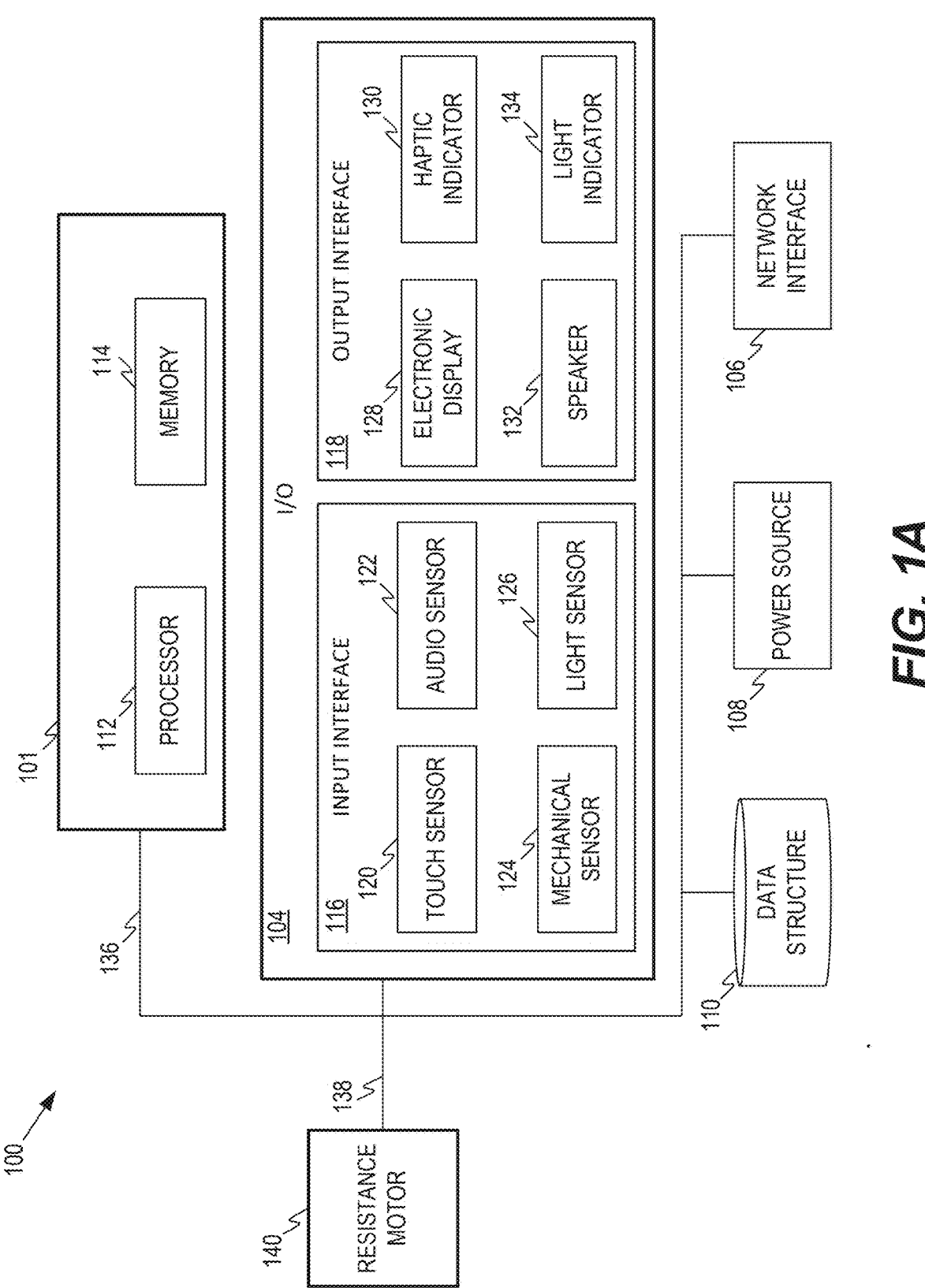
FIG. 1A is a schematic diagram of system architecture for an electronic exercise machine, consistent with some embodiments of the present disclosure.

Disclosed herein are systems, methods, and non-transitory computer readable media relating to performance of exercise routines, optionally using electronic exercise machines. Some disclosed embodiments relate to mechanical features of an electronic exercise machine. Some disclosed embodiments relate to software applications for using an electronic exercise machine. Some embodiments relate to a modular electronic exercise machine, allowing integration of a plurality of individual electronic exercise machines. Some disclosed embodiments relate to performance of exercise routines (e.g., with or without an electronic exercise machine). Some disclosed embodiments relate one or more combinations of mechanical features, software As another example, the cloud service may permit gamification of exercise routines. A user may initiate an exercise challenge and send the exercise challenge to other users of exercise machines via the cloud service. Each challenge recipient may be enabled to accept challenges and compete the exercise challenge asynchronously, e.g., at the challenge recipient's convenience. The cloud service may collect data from the initiator and each challenge recipient while performing the exercise challenge, and compare the data to determine performance results. The cloud service may notify the initiator and each challenge recipient of the results to permit an interactive exercise experience for remote users.

Some disclosed embodiments involve a computer vision (CV) system for facilitating a jumping challenging. The term "jumping" may refer to an action using at least the leg and/or foot muscles that pushes the body off a surface to lift the body into the air such that the feet are not in contact with the surface. A jump may involve both legs lifting the body vertically off the ground. Movements that may be associated with a jump may include a straight leg vertical jump, high knees jump (e.g., tuck), a burpee, split squats, air squats, and other jumping related activities.

While a number of the foregoing examples are described in connection with a cloud service, similar functionality may be achieved with disclosed embodiments by incorporating the various functions into the exercise equipment itself, into software paired with the exercise equipment, or through networking with another device or server that aids in providing the associated functionality.

Various terms used in this detailed description and in the claims may be defined or summarized differently when discussed in connection with differing examples. It is to be understood that the definitions, summaries, and explanations of terminology in each instance apply to all instances, even when not repeated, unless the transitive definition, explanation or summary would result in inoperability of an embodiment.

Throughout, this disclosure mentions "disclosed embodiments," which refer to examples of inventive ideas, concepts, and/or manifestations described herein. Many related and unrelated embodiments and examples are described throughout this disclosure. The fact that some "disclosed embodiments" are described as exhibiting a feature or characteristic does not mean that other disclosed embodiments necessarily lack that feature or characteristic.

This disclosure employs open-ended permissive language, indicating for example, that some embodiments "may" employ, involve, or include specific features. The use of the term "may" and other open-ended terminology is intended to indicate that although not every embodiment may employ the specific disclosed feature, at least one embodiment employs the specific disclosed feature.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions, or modifications may be made to the components illustrated in the drawings, and the illustrative methods described herein may be modified by substituting, reordering, removing, or adding steps to the disclosed methods. Accordingly, the following detailed description is not limited to the specific embodiments and examples but is inclusive of general principles described herein and illustrated in the figures in addition to the general principles encompassed by the appended claims.

Some embodiments described herein involve an exercise machine. An exercise machine may refer to a mechanical device that may be used to perform physical exercise. Examples of exercise machines may include wall-mountable resistance devices, free standing resistance devices, treadmills, stationary bicycles, elliptical machines, weight machines, other resistance machines, and/or any other machine designed to engage a user in physical exercise.

Some disclosed embodiments involve an electronic exercise machine. An electronic exercise machine may refer to an exercise machine including a resistance motor associated with electronics for controlling the resistance. The electronics may control an amount of resistance applied during a weightlifting exercise by regulating, for example, a level, a frequency, a duration, a speed, a duty cycle, a range of motion, an exercise type, an operational mode, and/or any other attribute associated with resistance applied by a resistance motor. In some embodiments, electronics, including for example, at least one processor, may control force applied by a resistance motor in response to one or more user inputs.

In some embodiments, an electronic exercise machine may be associated with a user interface. Such a user interface may include one or more of an electronic display, a touch-sensitive screen, a microphone, a speaker, a haptic interface, a light emitting diode (LED), one or more adjustable dials, knobs, buttons, switches, and/or levers and/or any other type of manipulatable control enabling user inputs and/or information display. For example, a user may provide one or more inputs via a user interface associated with an electronic exercise machine to initiate, select, modify, share, and/or terminate an exercise routine. Such an interface may initiate signals to at least one processor associated with an electronic exercise machine. In a similar manner, the at least one processor may transmit one or more signals to convey information via a user interface to a user of an electronic exercise machine.

Some disclosed embodiments involve an electromagnet. An electromagnet may refer to a temporary magnet created by intermittent electrical currents. For example, an electromagnet may be formed by passing an electrical current through an electrically conductive wire wrapped around a piece of magnetic metal to produce an electromagnetic field. Some examples of electrically conductive wires may include copper, steel, and/or aluminum wires. Some examples of magnetic metal may include cast iron, wrought iron, galvanized steel, ferritic and martensitic stainless steel. The strength of an electromagnetic field produced by an electromagnet may be increased, decreased, or terminated by controlling a level of electrical current through the wire. Electromagnetic fields produced by one or more electromagnets may be used to introduce resistance to mechanical motion. Overcoming such resistance may require an application of a mechanical force.

Some disclosed embodiments involve a motor (e.g., a resistance motor). Such a motor may include a one or more electromagnets configured to apply a variable electromagnetic field as resistance. For example, a level of resistance produced by a resistance motor may correspond to an amount of weight (e.g., "digital weight") needed to be overcome by muscles during performance of a weight-bearing exercise. A resistance motor may be associated with at least one processor configured to control a level of electrical current flowing therethrough, allowing the at least one processor to control attributes associated with resistance or digital weight produced by the resistance motor. In some embodiments, a resistance motor may be associated with a lower bracket configured to connect a bottom end of a vertical wall-mountable beam to a wall. For example, a resistance motor may be located inside a housing configured as a lower bracket for connecting a vertical wall-mountable beam to a wall. A lower bracket may be made of durable metal, such as stainless or galvanized steel, or aluminum.

Some disclosed embodiments involve an electronic wall-mountable exercise machine. An electronic wall-mountable exercise machine may refer to an electronic exercise machine including a frame (e.g., a vertically wall-mountable beam) for attachment to a wall via a plurality of supporting brackets. The frame and brackets may be made of durable metal (e.g., steel and/or aluminum) for sturdiness and may support a pulley system, allowing a first end of a cable to be connected to a resistance motor and a second end of the cable to be connected to exercise equipment. In some embodiments, an electronic wall-mountable exercise machine may include a user interface (e.g., including one or more adjustable dials, knobs, buttons, switches, and/or levers) allowing interaction with a controller of the wall-mountable exercise machine, e.g., to receive feedback and/or customize a workout to meet a fitness level and/or goal. For example, a dial may allow adjusting a resistance of a resistance motor, and a button may allow changing a direction and/or mode for exerting a force on a cable.

Some disclosed embodiments may involve a cable. A cable may include a rope, cord, chain, belt, and/or any other band or cordage having a tensile strength for withstanding repeated applications of tension. A cable may include a plurality of fibers (e.g., stainless and/or galvanized steel) that may be combined and twisted to form an elongated structure, and may optionally include a coating such as nylon and/or PVC to reduce friction and wear. In some embodiments, a cable may have a tensile strength suitable for withstanding a resistance force associated with a resistance motor of an electronic exercise machine. For instance, a first end of a cable may connect to a resistive motor and a second end of the cable may connect to a moveable arm of an electronic exercise machine, allowing for a mechanical force applied to move the arm to be at least partially resisted by the resistive motor.

Consistent with the present disclosure, an arm refers to an elongated structure. An arm of an exercise machine is an elongated structure that extends from the exercise machine to enable a user to apply exertions to the machine. In some embodiments, this may be enabled by a hollow within the arm for a cable associated with a pulley and connected to a resistance motor, such that exertion of a mechanical force via the cable (e.g., by a user of an electronic exercise machine exerting a force on the cable) may be at least partially resisted by the resistance motor. The arm of an electronic exercise machine may be adjustably associated with a vertically wall-mountable beam of the electronic exercise machine.

Some disclosed embodiments include at least one processor. "At least one processor" may involve any physical device or group of devices having electric circuitry that performs a logic operation on an input or inputs. For example, the at least one processor may include one or more integrated circuits (IC), including an application-specific integrated circuit (ASIC), microchips, microcontrollers, microprocessors, all or part of a central processing unit (CPU), graphics processing unit (GPU), digital signal processor (DSP), field-programmable gate array (FPGA), server, virtual server, or other circuits suitable for executing instructions or performing logic operations. The instructions executed by at least one processor may, for example, be pre-loaded into a memory integrated with or embedded into the controller or may be stored in a separate memory. The memory may include a Random Access Memory (RAM), a Read-Only Memory (ROM), a hard disk, an optical disk, a magnetic medium, a flash memory, other permanent, fixed, or volatile memory, or any other mechanism capable of storing instructions. In some embodiments, the at least one processor may include more than one processor. Each processor may have a similar construction, or the processors may be of differing constructions that are electrically connected or disconnected from each other. For example, the processors may be separate circuits or integrated in a single circuit. When more than one processor is used, the processors may be configured to operate independently or collaboratively and may be co-located or located remotely from each other. The processors may be coupled electrically, magnetically, optically, acoustically, mechanically, or by other means that permit them to interact At least one processor may include a single processor or multiple processors communicatively linked to each other and capable of performing computations in a cooperative manner, such as to collectively perform a single task by dividing the task into subtasks and distributing the subtasks among the multiple processors, e.g., using a load balancer. In some embodiments, at least one processor may include multiple processors communicatively linked over a communications network (e.g., a local and/or remote communications network including wired and/or wireless communications links). The multiple linked processors may be configured to collectively perform computations in a distributed manner (e.g., as known in the art of distributed computing).

Some disclosed embodiments involve a non-transitory computer-readable medium or a memory. Such terms may refer to any type of physical memory on which information or data readable by at least one processor can be stored. Examples include Random Access Memory (RAM), Read-Only Memory (ROM), volatile memory, nonvolatile memory, hard drives, CD ROMs, DVDs, flash drives, disks, any other optical data storage medium, any physical medium with patterns of holes, markers, or other readable elements, a PROM, an EPROM, a FLASH-EPROM or any other flash memory, NVRAM, a cache, a register, any other memory chip or cartridge, and networked versions of the same. The terms "memory" and "computer-readable storage medium" may refer to multiple structures, such as a plurality of memories or computer-readable storage mediums located within a wearable device or at a remote location. Additionally, one or more computer-readable storage mediums can be utilized in implementing a computer-implemented method. Accordingly, the term computer-readable storage medium should be understood to include tangible items and exclude carrier waves and transient signals.

Some disclosed embodiments involve a touch sensor. A touch sensor may include any type of equipment that captures and records physical touch or contact. Touch sensors, for example, may be capacitive and/or may include one or more of complementary metal-oxide-semiconductor (CMOS) integrated circuit (IC) chips, an application-specific integrated circuit (ASIC) controller and a digital signal processor (DSP) for sensing pressure, temperature, humidity, and/or any other indicator of touch. A touch sensor may convert an indication of touch to an electronic signal, which may be transmitted to at least one processor.

Some disclosed embodiments involve an audio sensor. An audio sensor may include any device that detects sound waves and coverts the sound waves into at least one electrical signal. An audio sensor may include, for example, one or more microphones. Some examples of such microphones include, unidirectional microphones, bidirectional microphones, cardioid microphones, omnidirectional microphones, onboard microphones, wired microphones, wireless microphones, or any combination of the above. The electronic signals from an audio sensor may be transmitted to at least one processor.

Some disclosed embodiments involve a mechanical sensor. A mechanical sensor includes any device that detects some sort of mechanical deformation or movement and translates that detection into an electrical signal. A mechanical sensor may be associated with a mechanical interface (e.g., a button, key, ball, switch, lever, touch pad, or dial) such that applying a mechanical force on the mechanical interface may cause the mechanical sensor to transmit a signal to at least one processor.

Some disclosed embodiments involve a light sensor. A light sensor may be included any device or be capable of detecting and converting optical signals in the near-infrared, infrared, visible, and ultraviolet spectrums into electrical signals. Examples of light sensors include photodetectors, photosensors, digital cameras, semiconductor charge-coupled devices (CCDs), active pixel sensors in complementary metal-oxide semiconductor (CMOS), or N-type metal-oxide-semiconductor (NMOS, Live MOS). The electrical signals may be used to generate image data. Consistent with the present disclosure, the image data may include pixel data streams, digital images, digital video streams, data derived from captured images, and data that may be used to construct one or more 3D images, a sequence of 3D images, 3D videos, or a virtual 3D representation. A light sensor may convert an optic signal to an electronic signal, which may be transmitted to at least one processor.

Some disclosed embodiments involve an electronic display. An electronic display includes any device or element capable of generating a visible image from electrical signals. For example, an electronic display may include a screen (e.g., LCD or dot-matrix screen), an electroluminescent (EL) display, a liquid crystal display (LCD), light-emitting diode (LED)-backlit Liquid crystal display (LCD), a light-emitting diode (LED) display, an organic light-emitting diode (OLED) display, an active matrix organic light-emitting diode (AMOLED) display, a plasma (P) display, a quantum dot (QD) display, and/or any other type of technology for rendering information visually. At least one processor may transmit signals to an electronic display to cause information to be displayed visually.

Some disclosed embodiments involve a haptic indicator. A haptic indicator may include any element or device that outputs vibrations or forces detectable to a human when in contact with a portion of the human body, such as a finger or hand. A haptic indicator may include, for example, a vibrating motor, linear actuator, vibrational transducer, or any other force feedback device that provide tactile or haptic cues or that is capable of converting an electrical signal into corresponding vibrations or force applications. At least one processor may transmit signals to a haptic indicator to cause information to be rendered haptically.

Some disclosed embodiments involve a speaker. A speaker may include any element or device capable of outputting sound. For example, a speaker may include one or more transducers for converting electromagnetic waves into sound waves. At least one processor may transmit signals to a speaker to cause information to be rendered as sound.

Some disclosed embodiments involve a light indicator. A light indicator may include any element or device that emits light in order to convey information. (e.g., indicating that a machine is powered on, indicating a mode of operation, indicating proper or improper usage, or indicating any other information. A light indicator may include a single light source (e.g., an LED), an array of light sources, (e.g., an LED array associated with different colors). At least one processor may transmit signals to a light indicator to cause information to be rendered visually.

Some disclosed embodiments involve a data structure. A data structure may include any collection of data values and relationships among them. The data may be stored linearly, horizontally, hierarchically, relationally, non-relationally, uni-dimensionally, multidimensionally, operationally, in an ordered manner, in an unordered manner, in an object-oriented manner, in a centralized manner, in a decentralized manner, in a distributed manner, in a custom manner, or in any manner enabling data access. By way of non-limiting examples, data structures may include an array, an associative array, a linked list, a binary tree, a balanced tree, a heap, a stack, a queue, a set, a hash table, a record, a tagged union, ER model, and a graph. For example, a data structure may include an XML database, an RDBMS database, an SQL database or NoSQL alternatives for data storage/search such as, for example, MongoDB, Redis, Couchbase, Datastax Enterprise Graph, Elastic Search, Splunk, Solr, Cassandra, Amazon DynamoDB, Scylla, HBase, and Neo4J. A data structure may be a component of the disclosed system or a remote computing component (e.g., a cloud-based data structure). Data in the data structure may be stored in contiguous or non-contiguous memory. Moreover, a data structure, as used herein, does not require information to be co-located. It may be distributed across multiple servers, for example, that may be owned or operated by the same or different entities. Thus, the term "data structure" as used herein in the singular is inclusive of plural data structures. A data structure may also include any hardware, software, firmware, or combination thereof for storing and facilitating the retrieval of information in the data structure.

Some disclosed embodiments involve a mobile communications device. A mobile communications device is a portable electronic instrument designed to facilitate information transmission to other devices or networks. Mobile communications devices may, for example, use cellular or other wireless and/or wired networks to transmit information such as voice and/or other data. For example, such transmissions may be in the form of voice calls, text messages, internet access, and application usage.

Mobile communications devices come in various forms, such as smartphones, tablets, laptop computers, IoT devices, wearable electronics (such as smart watches, smart rings, fitness trackers, smart glasses, smart clothing, smart jewelry, smart headphones, wearable digital assistants), and portable wireless hotspots. Depending on configuration and intended use, they may include features such as a touchscreen interface, a built-in camera, Wi-Fi, NFC, and/or Bluetooth connectivity, and GPS navigation.

Some disclosed embodiments involve a power source. A power source may include any element, device, or system for providing electrical energy to an electrical load or a circuit. Examples of power sources include one or more batteries (e.g., a lead-acid battery, a lithium-ion battery, a nickel-metal hydride battery, a nickel-cadmium battery), fuel cells, generators, capacitors, power converters, or connections (e.g., an electrical wall outlet) to an external source of electrical energy (e.g., an electric grid or other mechanism for supplying electricity). A power source may further include combinations of any of the foregoing.

Some disclosed embodiments involve a communications network. A communications network may include any type of physical or wireless infrastructure used to exchange data.

For example, a communications network may be the Internet, a private data network, a virtual private network using a public network, a Wi-Fi network, a LAN or WAN network, a combination of one or more of the forgoing, and/or other suitable connections that may enable information exchange among or between various system components. In some embodiments, a communications network may include one or more physical links used to exchange data, such as Ethernet, coaxial cables, twisted pair cables, fiber optics, or any other suitable physical medium for exchanging data. A communications network may also include a public switched telephone network ("PSTN") and/or a wireless cellular network. A communications network may be secured or unsecured network. In other embodiments, one or more system components may communicate directly through a dedicated communications network. Direct communications may use any suitable technologies, including, for example, BLUETOOTH™, BLUETOOTH LE™ (BLE), Wi-Fi, near field communications (NFC), or other suitable communication methods that provide a medium for exchanging data and/or information between separate entities.

A communications network may include a plurality of nodes interconnected via network infrastructure allowing encoded information to flow therebetween. Such network infrastructure may include, for example, one or more routers, switches, boosters, cables (e.g., Ethernet, coaxial cables, twisted pair cables, fiber optics, wires, buses), antennae, and/or any other wired and/or wireless computer networking technology configured for exchanging data.

Some disclosed embodiments involve a network interface. A network interface may include electronic circuitry and/or software code enabling at least one processor to communicate with another processor or processors via a network according to a communications protocol (e.g., Transmission Control Protocol/Internet Protocol or TCP/IP). Such circuitry may include, for example, at least one processor, a memory, one or more antennae configured to send and/or receive wireless signals from other devices, one or more wires and/or cables configured to send and/or receive wired signals from other devices, a plurality of physical and/or virtual ports, one or more software interface layers for implementing one or more communications protocols (e.g., lower layer protocols such as TCP, User Datagram Protocol (UDP), IP, and Internet Control Message Protocol (ICMP), and application layer protocols, such as Hypertext Transfer Protocol (HTTP), Secure Socket Shell (SSH), Transport Layer Security (TLS), and Secure Sockets Layer (SSL), and/or any other component required to enable networked communication between a plurality of computing devices.

Some disclosed embodiments involve a cloud service. A cloud service is a product that enables access to computing resources, such as servers, storage, and applications, over a network such as the internet. Cloud services are typically provided by third-party vendors who manage and maintain the underlying infrastructure allowing users to access and use the services via the internet. Non-limiting examples of types of cloud services, include Infrastructure as a Service (IaaS), Platform as a Service (PaaS), and Software as a Service (Saas). In some embodiments, a cloud service may execute program code instructions to implement one or more virtual machines.

In some embodiments, a communications network may be associated with a client-server model, allowing a cloud service to provide data storage and/or computational services to one or more client devices via the communications network. For example, a cloud service may store data and software associated with one or more electronic exercise machines and/or mobile communications devices (e.g., client devices) and/or execute program code instructions associated with using one or more electronic exercise machines. For example, a cloud server may store data and/or execute program code instructions for implementing a plurality of operational modes for an electronic exercise machine (e.g., in association with one or more exercise routines), creating an interface between a mobile communications device and one or more electronic exercise machines, and/or pairing two or more modular electronic exercise machines.

As another example, a cloud server may store data and execute program code instructions associated with performances of exercise routines (e.g., with or without an electronic exercise machine). For example, a cloud server may store results or achievements and/or provide feedback associated with performances of exercise routines (e.g., by a single or by multiple users), provide instructions for using an electronic exercise machine and/or for implementing differing modes of operation of an electronic exercise machine, facilitate interactions between remote users performing exercise routines (e.g., with or without an electronic exercise machine), and/or provide any other service associated with performances of exercise routines.

Some disclosed embodiments may involve signals. Signals may refer to an electrical or electromagnetic wave that carries information such as voice, video, or data. Signals can take various forms, including analog signals and digital signals. Other signal examples include radio signals, optical signals, microwave signals, infrared signals, ultrasonic signals, or any other wave or other conveyance that carries information. Non-limiting examples of signals include signals in the electromagnetic radiation spectrum (e.g., AM or FM radio, Wi-Fi, Bluetooth, radar, visible light, lidar, IR, Zigbee, Z-wave, and/or GPS signals), sound or ultrasonic signals, electrical signals (e.g., voltage, current, or electrical charge signals), electronic signals (e.g., as digital data), tactile signals (e.g., touch), and/or any other type of information encoded for transmission between two entities via a physical medium.

Some disclosed embodiments involve an indication. An indication may include a measurement, sign, and/or a signal conveying information about a state and/or level of a physical phenomenon. For example, an indication may signal the presence, occurrence, or status of something. An indication may be provided in a form that can be detected by a person or a system. For example, computers or other electronics may detect indications through signals, and humans may detect indications through light, audio, haptics, odor, or taste. In some instances, electronic sensors can also detect indications through light, audio, haptics, and odor, as well as through substance or image sensing.

Some disclosed embodiments may involve a mode of operation. A mode of operation refers to a way in which something works. For example, a device or system may work in a number of different ways, depending on a mode selection. A mode of operation may, by way of example, refer to a manner and/or a set of conditions for performing one or more procedures. A mode of operation may tune or adjust an operation of a system to accommodate a particular set or range of conditions. For instance, a first mode of operation may be associated with a first set of conditions and a second mode of operations may be associated with a second set of conditions, where the first mode of operation may be incompatible with the second set of conditions, and the second mode of operation may be incompatible with the first set of conditions. However, modes need not be incompatible. In some instances, a mode reflects a use preference, and the mode may be changed when preferences change.

FIG. 1A is a block diagram of exemplary system architecture of an electronic exercise machine, consistent with some embodiments of the present disclosure. It is to be noted that FIG. 1A is a representation of just one embodiment, and it is to be understood that some illustrated elements might be omitted, and others added within the scope of this disclosure. For example, some elements of FIG. 1A may be grouped and/or housed separately. In some embodiments, circuitry associated with a resistance motor of an electronic exercise machine may be housed and/or positioned separately from at least one processor configured to control settings for operating the electronic exercise machine (e.g., a control unit may be located in proximity to a resistance motor and at least one processor may be located elsewhere, and may be in electronic communication with the control unit). While housed and/or located separately, the control unit and the at least one processor may be in communication via wired and/or wireless means. For example, a user may set a desired resistance weight via a software application installed on a mobile communications device. The mobile communications device may transmit an indication of the desired resistance weight to at least one processor. Based on the indication, the at least one processor may transmit a control signal to the control unit to cause the resistance motor to apply the desired resistance weight.

System architecture 100 may include a control circuit 101, an I/O (input-output) unit 104, a network interface 106, a power source 108, and a data structure 110. Control circuit 101 may include at least one processor 112 and a memory 114. I/O unit 104 may include an input interface 116 and an output interface 118. Input interface 116 may include one or more of a touch sensor 120, an audio sensor 122, a mechanical sensor 124, and a light sensor 126, and/or any other type of sensor configured to receive an input. Output interface 118 may include one or more of an electronic display 128, a haptic indicator 130, a speaker 132, one or more light indicators 134, and/or any other type of output interface. Control circuit 101, I/O unit 104, network interface 106, power source 108, and data structure 110 may be interconnected via bus system 136. Control circuit 101 may be connected to a resistance motor 140 via one or more wires and/or cables 138. In some embodiments, one or more components of control circuit 101 may be located inside a housing encasing resistance motor 140, however this is not required.

For example, upon receiving a selection of an exercise routine to be performed using an electronic exercise machine via input interface 116, at least one processor 112 may retrieve data from memory 114 associated with the selected exercise routine. Such data may include, for instance, settings, preferences, a history of prior performances of the selected exercise routine, and/or any other data associated with the selected exercise routine. The at least one processor 112 may apply the retrieved data to control a current supplied to resistance motor 140, to thereby control the resistance applied by resistance motor 140 during performance of the selected exercise routine.

Figure 1B:
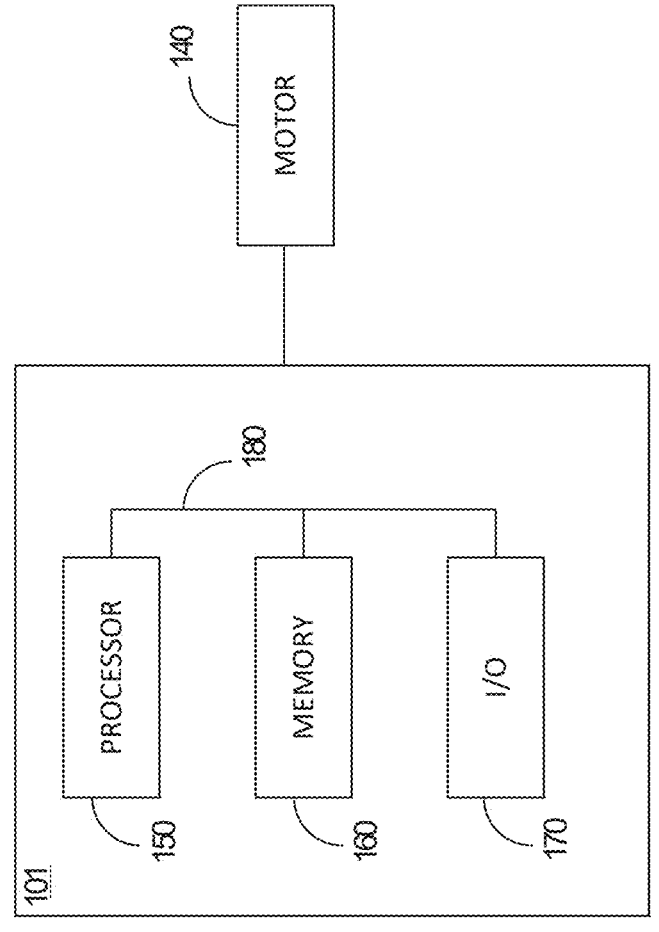
FIG. 1B is a block diagram of a controller for controlling an electronic exercise machine, consistent with some embodiments of the present disclosure.

FIG. 1B is a block diagram of a controller for controlling an electronic exercise machine, consistent with some embodiments of the present disclosure. Components of FIG. 1B may be similar in description to the corresponding components of FIG. 1A. A controller 101 of a exercise machine 200 may include at least one processor 150, at least one memory 160, and an input output (I/O) 170) connected via a bus system 180. I/O 170 may include wired and/or wireless (e.g., one or more antennas) communications means enabling electronic communication between at least one processor 150 and another processor and/or device via a communications network. For instance, at least one processor 150 may communicate with mobile communications device 224 and/or another at least one processor 150 configured with another instance of an exercise machine 200 via an interface such as I/O 170. In some embodiments, at least one processor 150 may communicate with a wearable extended reality appliance via I/O 170. Some or all of controller 101 may be located within a motor housing, while some elements such as at least one processor 150, at least one memory 160, input output (I/O) 170, a bus system 180 may be encased within other portions of the equipment.

FIG. 2 is a block diagram of an exemplary method for assessing the surface plane (e.g., for a floor, platform, stage, table top), consistent with some disclosed embodiments. For example, the surface plan may be assessed using one or more 3D images acquired by a camera 175 (such as camera 175 in FIG. 8). It is to be noted that the method is intended as illustrative only and does not limit the disclosure to any implementation details, and other methods for assessing the surface plan may be used.

In Step S202, a depth image including the surface is acquired. For example, CV engine 115 may receive at least one 3D image of the surface region from camera 175 (e.g., including a 3D camera).

In Step S204, the lower part of a depth image may be identified where the surface is expected to be located (e.g., at the bottom part of the image).

In Step S206, each pixel in the lower part of the depth image may be projected to world coordinates, resulting in a 3D world point for each pixel in the surface region of the depth image.

In Step S208, assume that only the surface is seen and associated the point cloud with a Euclidian plane (e.g., according to an equation such as $a*x+b*y+c*z+d=0$, in which case a good estimation of the $[a,b,c,d]$ parameters may lead to small residual error). The term "point cloud" may refer to a set of data points in space, optionally representing a 3D shape or object. Each point position may be associated with a set of Cartesian coordinates (X, Y, Z). Point clouds may be produced by 3D scanners or by photogrammetry software measuring many points on the external surfaces of objects around them. A point cloud may be the output of a 3D scanning processes. Point clouds may be converted to other formats associated with image processing, such as polygon mesh or triangle mesh models, NURBS surface models, or CAD models through surface reconstruction.

In Step S210, remove outlying and non-relevant points (e.g., associated with the body of the jumper, chairs, and other objects positioned on the surface), for example using image processing techniques, such as a RANSAC algorithm, clustering, least squares regression cubic spline. [AVIAD]

Steps S204 through S210 may be repeated with an increasing minimal set of points to capture a greater ratio of valid pixel associated with the surface and avoid locking into a surface that is not a part of the surface.

In Step S212, the orientation of the plane may be adjusted (e.g., normalized) to be horizontally flat and face upwards.

FIG. 3 is a schematic illustration of a cloud service 300 associated with wall-mountable electronic exercise machine 200, consistent with some embodiments of the present disclosure. Cloud service 300 includes at least one server 303 (e.g., including at least one processor), and a data structure 305 connected to a communications network 185. Cloud service 300, wall-mountable electronic exercise machine 200 and mobile communications device 224 may communicate via a communications network 185. In some embodiments, communications network 185 may include a dedicated communications network, such as a Bluetooth communications channel connection mobile communications device 224 with at least one processor 112 of electronic exercise machine 200. In some embodiments, a light sensor (e.g., a camera) associated with mobile communications device 224 may capture images (e.g., of a user performing an exercise routine with or without wall-mountable electronic exercise machine 200). Cloud service 300 may store and analyze the images or videos, for example, to allow a first user of a first instance of wall-mountable electronic exercise machine 200 compete with a second user (e.g., of a second instance of wall-mountable electronic exercise machine 200), to provide feedback and/or instructions to a user performing an exercise routine, and/or provide any other service associated with performances of exercise routines (e.g., with or without wall-mountable electronic exercise machine 200).

As shown in FIG. 3 some embodiments include an electronic exercise machine 200. FIG. 2A is a perspective view of an exemplary wall-mountable electronic exercise machine 200, consistent with some embodiments of the present disclosure. Electronic exercise machine 200 may include a vertically wall-mountable beam 202, one or more resistance motor 140, a control circuit (e.g., see FIG. 1A) and/or controller 101 (e.g., see FIG. 2A), and/or a computing device 105 (e.g., see FIG. 8), a cable 206, at least one arm 212, a rotatable shoulder 214, and a control knob or dial 216. Resistance motor 140 may be located within or attached to beam 202.

Cable 206 may run substantially along the length of vertically wall-mountable beam 202 from motor 140 to rotatable shoulder 214 and through arm 212, ultimately connecting to an exercise accessory 222, such that a pulling force applied to exercise accessory 222 may be at least partially resisted by resistance motor 140 via cable 206. A height of arm 212 may be adjusted, and rotatable shoulder 214 may allow adjusting an angle of arm 212 relative to vertically wall-mountable beam 202. At least one processor 112 of control circuit 101 may transmit one or more signals to control a level of current flowing through resistance motor 140, thereby controlling a level of resistance applied by resistance motor 140 onto cable 206.

A control knob such as dial 216 may provide a user interface allowing a user to engage in electronic communication with wall-mountable electronic exercise machine 200. Dial 216 may be associated with I/O unit 104. For example, a user may use dial 216 to adjust one or more operational parameters and/or attributes associated with a resistance applied by resistance motor 140 onto cable 206. At least one processor 112 of control circuit 101 may receive an indication of an attribute selection via dial 216 from I/O 104 and may transmit a signal causing an adjustment to a current or a voltage flowing to resistance motor 140, to thereby cause resistance motor 140 to apply resistance characterized by the selected attributes to cable 206.

In some embodiments, at least one processor of exercise machine 200 may pair to a mobile communications device 224. Mobile communications device 224 may be configured with a user interface associated with wall-mountable electronic exercise machine 200, allowing a user to engage in electronic communication with at least one processor of wall-mountable electronic exercise machine 200 via a communications channel. For example, a user may use mobile communications device 224 to adjust a resistance and/or receive an indication of resistance applied by resistance motor 140 onto cable 206, change a mode of operation wall-mountable electronic exercise machine 200, receive updates and/or a report associated with an exercise routine performed using wall-mountable electronic exercise machine 200, as described in greater detail herein.

In some embodiments, an electronic exercise machine and/or a paired mobile communications device 224 may communicate with an associated cloud service via a communications network. For example, the cloud service may include a server and a data structure configured to provide data and/or processing services associated with operating an electronic exercise machine, and/or for with performances of one or more exercise routines (e.g., with or without an electronic exercise machine).

In some embodiments, user-initiated challenges can be sent to other electronic exercise equipment users to gamify working out on their electronic exercise equipment. Challenge recipients may be able to accept challenges and compete asynchronously at the challenge recipient's convenience. Collected data from the exertions of the initiator and the recipient may then be compared, and the participants may be notified of the results.

Some disclosed embodiments involve the performance of asynchronous user initiated and cloud mediated exertion challenge operations. A challenge refers to a task or objective, in a competitive context, that is presented to an individual or group of individuals. An exertion challenge refers such a task or objective involving physical effort. Exertion challenge operations refer to steps for facilitating the presentation or acceptance of an exertion challenge. For example, the physical effort may involve performing one or more exercises, lifting weights, or performing other physical manipulations. In the context of physical fitness, an exertion challenge may involve lifting, pressing, or moving a particular amount of weight associated with a particular exercise, performing a series of repetitions of an exercise (with or without weight resistance) or performing a combination of related or unrelated exertions. The challenge may or may not involve a time limit (e.g., perform ten 200 lbs. bench presses; perform ten 200 lbs. bench presses in 20 seconds; or fastest time to perform ten 200 lbs. bench presses.)

An exertion challenge is "user initiated" if a user starts or proposes to start the challenge. Operations are cloud mediated when a network, such as the Internet is used to facilitate or enable an exertion challenge. For example, a first user may present a challenge to a second user or to a group of users via an application that transmits the exertion challenge over a network, such as the Internet. In this example, the exertion challenge is cloud mediated. Similarly, the first user may receive feedback via the network in the form of an acceptance of a challenge or in the form of information about the performance of others who accepted the challenge. These too are examples of cloud mediation.

Asynchronous challenges refer to challenges that do not necessarily occur simultaneously or in real-time. For example, a first user may perform activities for initiating an exertion challenge at one time, and another user may perform exertion activities in response at another time. The fact that users are able to compete by performing their challenge-associated activities at differing times (e.g., minutes, hours, or even days later depending on the challenge) is an example of asynchronicity.

With some disclosed embodiments the performance of each user participating in an exertion challenge be by compared and/or ranked. In this way, users may gamify their exercise experience without requiring challengers to be present at their equipment at the same time.

In one example, a user may initiate an exertion challenge against at least one other user to better motivate an exercise routine. To initiate an exertion challenge, a user may operate one or more user interfaces or controls associated with exercise equipment or may operate a communications device such a cell phone paired with the exercise equipment. An associated command that may be recognized by one or more processors as an instruction to challenge another user. In some embodiments, a user may initiate an exertion challenge via an application of a computing device in communication with one or more processors of the exercise equipment, such as a mobile device with a mobile application.

Some embodiments may involve a jumping challenge. The term "jumping challenge" may refer to a competition comparing multiple jumps, e.g., of a single jumper at different times, or a comparison of one or more jumps performed by multiple jumpers. For example, the challenge may measure one or more of: the number of qualifying jumps performed within a predetermined time frame, the maximum height reached by each jumper, the average height of the qualifying jumps performed by each jumper, the accumulated height of the qualifying jumps performed by each jumper (e.g., jump as high as Mt. Everest), the frequency of the qualifying jumps (e.g., the maximum number of jumps within a time frame), the speed of a jump (e.g., the longest and/or shortest jump), the precision of the jump (e.g., landing form), and any other measure related to jumping. Additionally, a jumping challenge may refer to an exercise where a single jumper jumps to achieve a score, ranking, or other measure of success. In some embodiments prior to initiating a jumping challenge, a CV engine 115 (see FIG. 8) may estimate the surface plane (e.g., the floor on which the jumpers are standing when performing jumps). In some embodiments, the surface plan may be estimated using a 3D point cloud generated from images acquired by camera 175.

Some disclosed embodiments may mediate the exertion challenge operations via the cloud. In some embodiments, a cloud server may be in communication with exercise equipment associated with a first and second user. In some embodiments, first and second users may be associated with different exercise equipment machines, and in some embodiments, they may be associated with the same exercise equipment machine. Cloud mediated challenges may involve a cloud server (e.g., a physical or virtual computer server) configured to gather, process, and/or compare data from one or more sensors or exercise equipment machines. The cloud server may mediate challenge operations between users by serving as a gateway between the users. In some embodiments, such a cloud server may act as data processor, comparator, and/or analyzer to collect and analyze data from multiple exercise equipment machines or sensor to judge the challenge.

In some embodiments, a cloud server may be a virtual server that runs on a cloud computing infrastructure. Instead of being hosted on a physical server in a traditional data center, a cloud server may be provisioned and managed in a virtualized environment provided by a cloud service provider.

Figure 8:
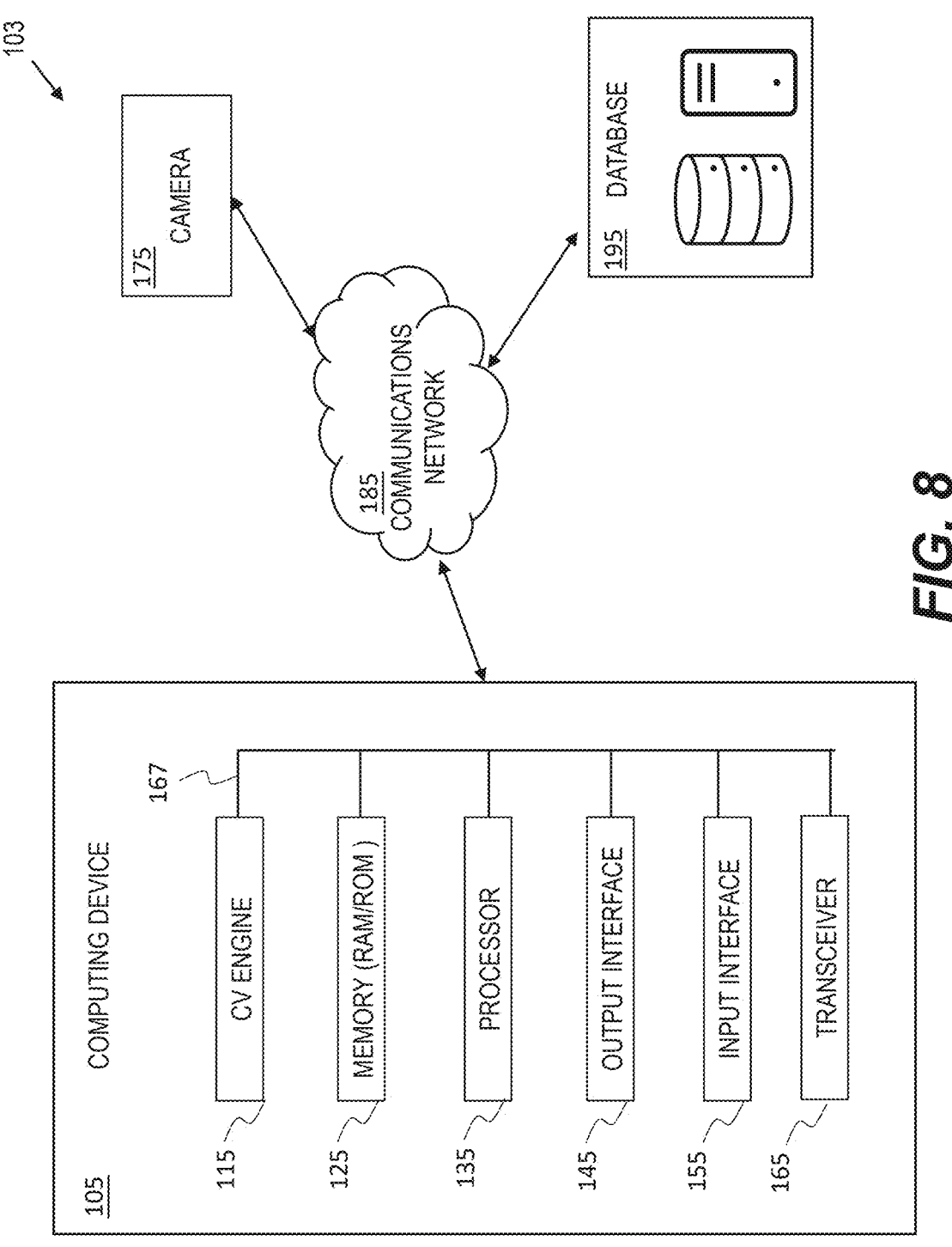
FIG. 8 is a block diagram of an exemplary implementation of a computer vision (CV) jump competition system.

In some exemplary embodiments, as shown in FIG. 8, communications network 185 may include wired and/or wireless communications means, such as any combination of wires, cables, fibers, and/or transceivers configured for analog and/or digital communication.

Some disclosed embodiments involve capturing via at least a first sensor first sensor data reflecting a first subject performing a first exertion. As used herein, the term sensor refers to a detector the output of which reflects exertion of an individual. Examples of sensors include image sensors, motion sensors, load cell sensors, speed and distance sensors, pressure sensors, torque sensors, or any other sensor capable of outputting data reflective of one or more metrics of a user's performance during a human exertion. An exertion refers to a physical activity. For example, an exertion may be associated with an exercise, lifting weights, or other physical manipulation involve lifting, pressing, or countering a resistance. In exertions involving a source of resistance, the source of resistance may be weights, an electronic brake (e.g., a motor), a stretchable band, a mechanical device, or weight of a human body. Exertions do not necessarily require a particular source of resistance. For example challenges involving, jumping, sit-ups, push-ups, planks, and others are not associated with external sources of resistance.

Figure 3A:
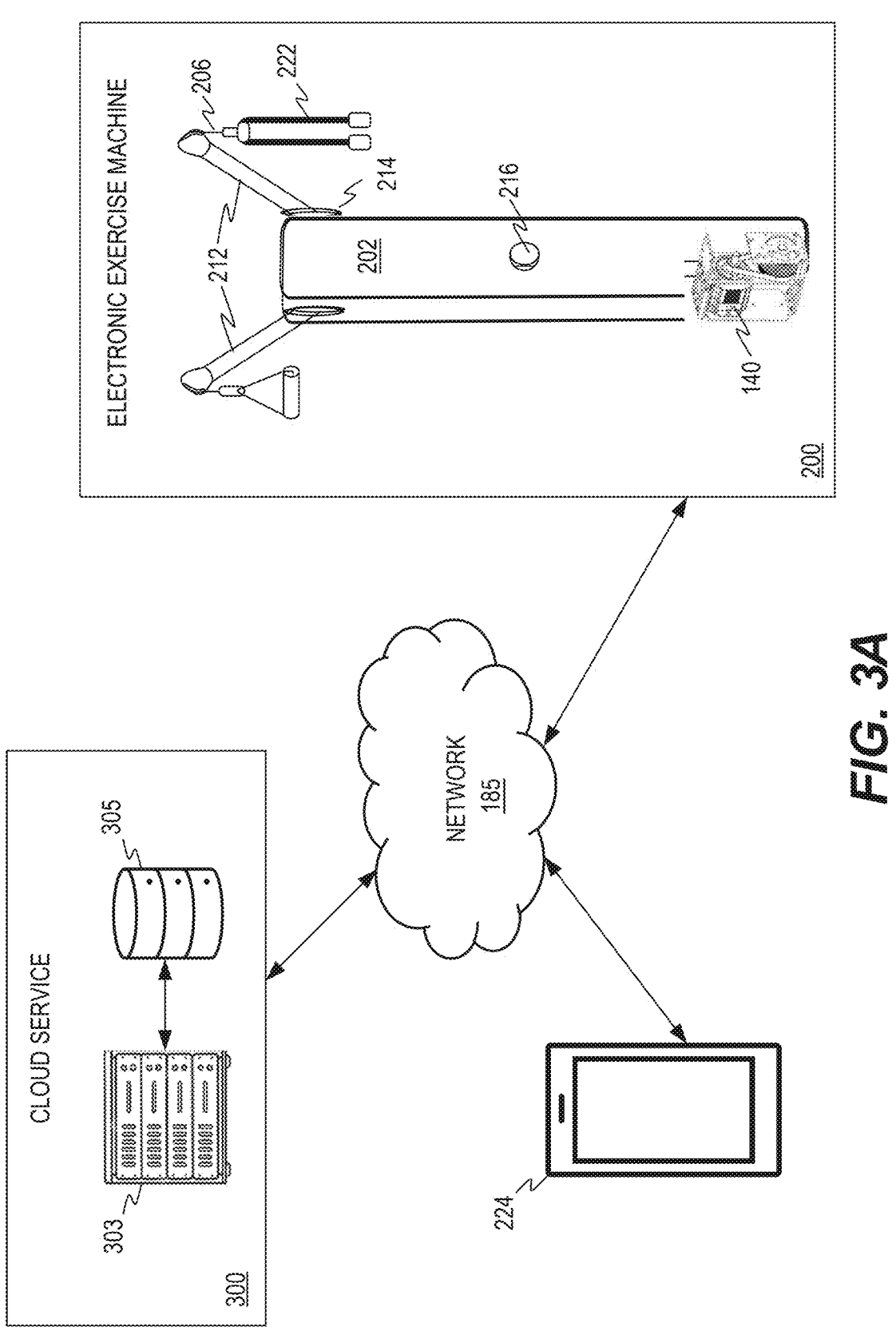
FIG. 3A is a schematic network diagram, consistent with some embodiments of the present disclosure.

In some embodiments, at least a first sensor may be integrated into piece of exercise equipment. For example, one or more sensors in exercise machine 200 in FIG. 3A may sense a force applied to a cable and might also sense a distance the cable travels, cable velocity and/or cable acceleration. As shown in FIG. 3A, resistance may be supplied by a motor 140, and the sensor might be part of motor controller that regulates a resistance applied by the motor to a cable 206 spooled to the motor. The motor's resistance may simulate a weight on the cable as a user performs an exertion by applying force to an accessory 222 at the end of the cable. The travel sensor may be used to determine if the user completed a full repetition. For example, a successful repetition may be defined for a particular exercise as at least 0.75 m of cable pull. The travel sensor may determine if such a threshold is met.

Figure 12C:
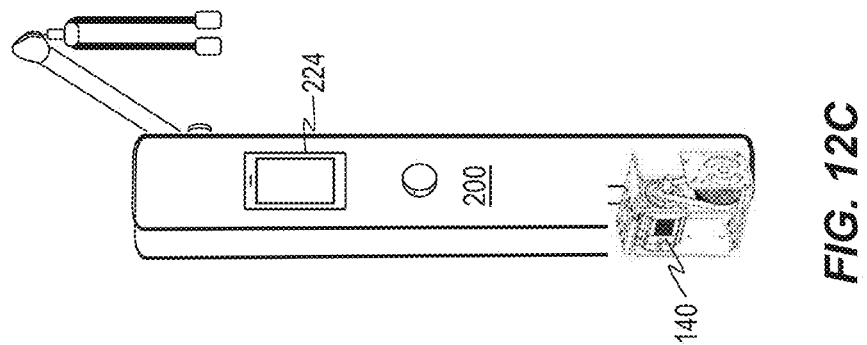
FIGS. 12A-12C are illustrations of three exemplary sensing setups consistent with some disclosed embodiments.
Figure 12B:
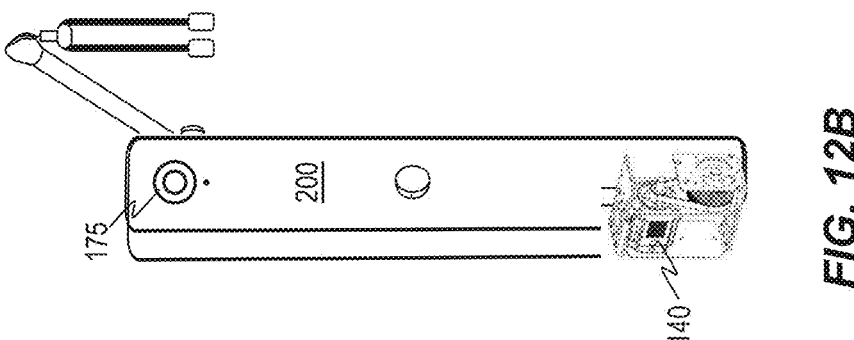
Figure 12A:
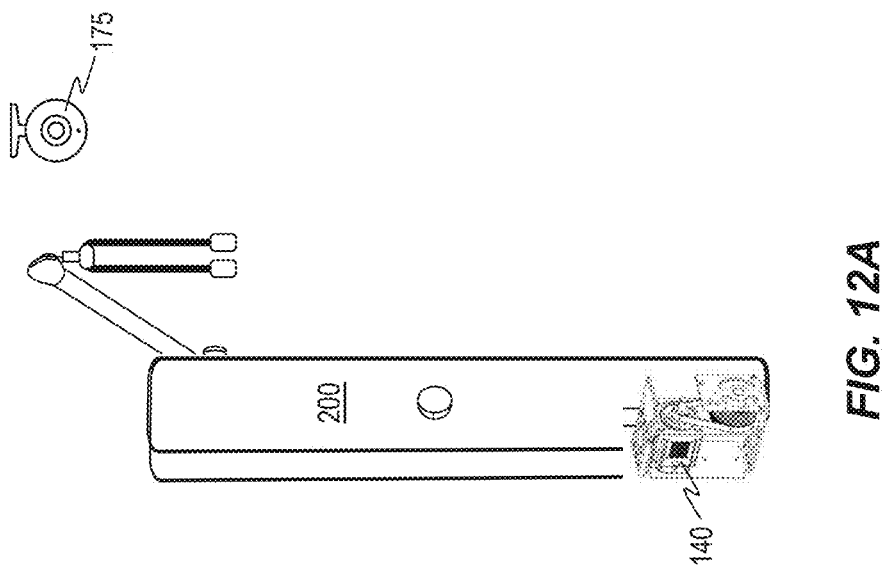

In some embodiments the at least a first sensor may include an image sensor. In some embodiments, the sensors in FIGS. 12A-12C may include camera 175 and/or a sensor of mobile communications device 224. The image sensor may be used to determine if the user properly performs an exertion or exercise (e.g., if the user applies a proper form). While an image sensor is not required in all embodiments, when employed, it can be manifest in at least one of three forms, as illustrated in FIGS. 12A-12C. In FIG. 12A, the image sensor is a separate device, paired with the exercise equipment or paired with another device used to monitor exercises. Image sensor 175 may be mounted on a ceiling or wall, or placed on a table or on the floor for monitoring exercise form. It may be supplied with the exercise equipment or may be supplied by the user. Image sensor 175 in FIG. 12B is integrated into exercise machine 200. It may be pre-aimed toward an expected area of the user, or it may track the user. In FIG. 12C, an image sensor in the user's smart phone or other mobile communications device 224, may be used with the exercise machine to monitor the user's form.

In some embodiments, as shown in the example in FIG. 8, a camera 175 may include one or more optical detectors (e.g., CMOS/CCD sensors) configured with one or more 2D cameras and/or 3D cameras. In some embodiments, camera 175 may include at least one processor, and at least one transceiver, e.g., for transmitting images at least to database 195 and CV engine 115. Database 195 may store information relating to a jumping challenge, such as personal information associated with each jumper competing in the jumping challenge, the criterion defining a qualifying jump, and a history of scores of jumpers who already participated in a particular jumping challenge. The term "qualifying jump" may refer to a jump that meets one or more predefine criteria. For example, a qualifying jump may be a vertical jump that elevates the body such that the minimal distance between the jumper and the surface exceeds a predefined height. Additionally, or alternatively, a qualifying jump may be defined as the jumper separated (e.g., not in contact) with the surface for a predefined time duration. In some embodiments, the closest distance between the jumper and the surface may be used as a determining criterion, e.g., to account for the jumper twisting and/or bending his body. In some embodiments, the distance between the head and the surface may be used as a determining criterion. In some embodiments the distance between the center-of-mass and the surface may be used as a determining criterion. In some embodiments a combination and/or average of different points on the jumper (e.g., key points) may be used as a determining criterion. The information may be stored according to a structure, such as one or more hierarchical tables, linked lists, trees, stacks, queues, objects, relationships (e.g., as a semantic database), or any other data structure. The database structure may allow retrieving information from the database via query.

In some embodiments, the first exertion includes a series of exertion repetitions. A series refers to a sequence or progression. As used herein, a series of exertion repetitions may involve a repetition of a same exertion of an exercise a certain number of times, or a sequence or progression of a combination of a plurality of exertions repeated in order. For example, the series of exertion repetitions may include multiple repetitions of a pulling exertion. Alternatively or additionally, it may include a repetition of a pulling and a release of the pulling as a same exertion. As another example, the series of exertion repetitions may include a pulling exertion, followed by an exertion of rotating arms.

In some embodiments. the first sensor data reflects at least one parameter associated with the first exertion. A parameter is a characteristic or measure. Thus, a parameter associated with an exertion is some characteristic or measure of the exertion. Sensor data reflects at least one parameter by containing information associated with the at least one parameter, providing data that observes or corresponds to the at least one parameter, or providing data representative of the at least one parameter. The at least one parameter may be indicative of a particular movement associated with the exertion or one or more settings of the exercise equipment associated with the exertion. Non-limiting examples of the at least one parameter may include a force or force range of an exertion, a duration of an exertion, a direction of exertion (relative to the exercise equipment, the floor, the user, or any other fixed point), extent of an exertion (e.g., a length of cable pulled) a form of an exertion (e.g., whether the user met threshold form criteria during the exertion), or any other measurable factor associated with the exertion.

In some embodiments, the at least one parameter associated with the first exertion includes a particular type and a particular form of the first exertion. A particular type of the exertion refers to a classification or categorization of exertions based on shared characteristics, properties, or traits. Non-limiting examples of particular types of exertions include a pushing movement, a pulling movement, a relative intensity level such as low intensity exertions or high intensity exertions, and any other differentiating characteristics of exertions. A particular form of the exertion refers to a specific technique or manner the exertion is performed. For example, a form may be associated with a proper alignment of the body during an exertion, movement patterns of the exertion, and/or execution of the exertion to maximize effectiveness and minimize a risk of injury. As a non-limiting example, a particular form of a squat exertion may be associated with the user's feet being shoulder width apart, toes turned slightly outward, and lowering the body by bending at the hips and knees, such that the knees align with the toes, the chest stays lifted, and the back remains straight.

In some embodiments, the particular exertion type may include an exercise category. Examples of categories include muscle groups, body focus (e.g. upper body, lower Body, core, etc.), cardiovascular, resistance related, accessory related, or any other grouping or classification. In some embodiments, exercise categories are associated with a goal of the exercise, muscles the exercise focuses on, a difficulty level, time/metric parameters, popularity of the exercise, a standard that is used in the industry to categorize exercises, or any other suitable classification that differentiates exercises. Exercise categories may include, for example, aerobic or cardiovascular exercises that improve cardiovascular fitness and endurance by elevating the heart rate and increasing oxygen consumption, strength training or resistance exercises that aim to strengthen muscles, flexibility exercises that aim to improve joint range of motion or muscle elasticity, balance and stability exercises that focus on the body's ability to maintain equilibrium and control movements, high-intensity interval training exercises that involve short bursts of intense exercise alternated with periods of rest, functional exercises that mimic movements and activities of daily life or specific sports, low-impact exercises that focus on being gentle on the joints and minimize stress on the body, sports-specific exercises that are specific to a specific sport or athletic activity, and any other categories associated with a particular focus of exercise goal or target muscle group.

In some embodiments, the particular exertion form included in the at least one parameter includes a posture. A posture refers to an alignment and positioning of the body's various parts in relation to each other, in relation to the exercise equipment, and/or in relation to the user's surrounding environment. Posture is associated with spinal alignment, muscular balance, and optimal movement and function. Some embodiments may include a posture in the at least one parameter by defining a particular alignment of the head, next, spine, shoulders, arms, legs, hips, and/or other body parts. In some embodiments, a user's posture may be implemented in the at least one parameter by monitoring a posture of the user using image data or sensor data indicative of the user's body position, balance, weight distribution, acceleration vector, and other sensors or data associated with the user's alignment and body positioning.

In some embodiments, the particular exertion form may include one or more other pieces of information such as a movement range, a velocity, an acceleration, a duration, number of repetitions, or one or more other parameters that may indicate the quality of the exertion done by the subject. In some embodiments, the particular exertion form may include a minimum level of exertion such as a minimum or threshold amount of resistive force to perform the exertion, or one or more other pieces of information including, for example, a minimum travel distance/angle, a minimum level of acceleration, a minimum level of acceleration, a minimum duration of time, or a parameter at a level that may indicate a threshold level of acceptable exertion.

In some embodiments, the first sensor data may reflect a degree of completion of the first exertion and/or a quality of the first exertion. In some embodiments, the degree of completion may indicate the quality of the exertion. In some embodiments, one or more processors may determine the degree of completion by analyzing the movements of the arm(s) of the exercise machine. Such movements may include a moving speed, an acceleration, a start/stop angle, a steadiness, a frequency (as of between repetitions,) an on/off time ratio (as indicator of rest time between sets,) and/or any quantifiable parameter that may indicate the user's easiness to finish an exercise. For example, high quality exertions may be indicated by, for example, by repetitions that meet criteria for an amount of cable travel when a particular minimum or predefined resistance is applied to the cable. If an image sensor is employed, high quality exertions may also be indicated by image analysis indicating compliance with form requirements. Other indicators of high quality exertions may include one or more of detected steady and consistent controlled movement, stable repetition frequencies, short on/off time ratios, short breaks between sets, minimized shaking, and/or a maintained threshold related heart rate throughout the scheduled exercise. In contrast, incomplete, unstable, and/or inconsistent arm movements, range/angle not meeting requirements, taking long breaks between sets, shaking, and/or detected out of range high heart rate may indicate a low quality of the exertion/low degree of completion of the exertion. These parameters may be detected using one or more of the sensors discussed herein.

In some embodiments, the first sensor data may include outputs of one or more resistive motors. A resistive motor includes any motor that can be controlled to provide a resistive force. Outputs of one or more resistive motors refers to data that may be collected from at least one sensor measuring at least one characteristic of a resistive motor such as, for example, an amplitude, a frequency, a phase, a timing (e.g., on/off), a direction, a torque, an extent of rotation, a power output (such as Watts or horsepower), and/or any other measurable characteristic of an electrical resistance motor and/or an electromagnetic signal associated with a resistive motor output. In some embodiments, the first sensor data may correspond to motions of a cable, and include at least two of cable length pulled, cable velocity, a time interval between cable pulls, and an overall duration of the set of exertions performed by the first subject. Cable velocity refers to a speed of the cable exiting or retracting into the exercise equipment. A time interval between cable pulls refers to a length of time between a first instance that the cable is fully abducted from the exercise equipment for a first repetition of the exertion, and a second instance that the cable is fully abducted for a second repetition of the extraction. In some embodiments, the time between cable pulls may refer to a period of time that the cable is retracted into the machine between abductions. In such embodiments, one or more cables may be attached to the one or more resistive motors, and the first sensor data may be measured by a sensor associated with part of the motor, the cable, or both. In some embodiments, the sensor may be a processor or part of a processor that receives electrical signals from the motor and is able to ascertain parameters based on analysis of the electrical signals.

In some embodiments, the first sensor data may further include an output of one or more an associated image sensors. In some embodiments, the image sensors may include one or more digital imaging sensors in a camera system that communicate with a processor of the exercise equipment, such that one or more data transmitters of the camera system are capable of transmitting captured image data to one or more processors (e.g., the processor 112, or a different processor) for image processing. By way of example, as previously discussed, FIG. 12A illustrates a camera device 175 that may be positioned separate from the exercise equipment 200. For example, camera device may be mounted to a ceiling, wall, or piece of furniture in the room where exercise equipment 200 is located. In such embodiments, camera device 175 may capture and transmit captured image data to one or more processors associated with exercise equipment 200. In some embodiments, the one or more associated image sensors may be embedded in or attached to the exercise equipment, such as the example shown in FIG. 12B. As shown, an attached image sensor 175 may collect image data while a user operates exercise equipment 200. In some embodiments, the one or more associated image sensors may be part of a computing device such as mobile communications device (e.g., a mobile phone) in communication with one or more processor of the exercise equipment. Referring to FIG. 12C, a mobile communications device 224 may capture image data of the user and provide the image data to one or more processors associated with exercise equipment 200.

In some embodiments, an input is received to convert the first sensor data into a challenge. Converting first sensor data into a challenge involves determining exertions based on the first sensor data and conveying related information to at least one other user to challenge that other user. An input received to convert the sensor data into a challenge may include an action by the first user. For example, the user may respond to a prompt to initiate a challenge. That response may occur before, during, or after the exertions that form the basis for a challenge. In one example, after the user performs a series of exertions, the user may cause an application to present the performance as a challenge to one or more others. The presentation of the challenge may indicate a goal or level that needs to be surpassed to win the challenge. For example, if a user performs ten 150 lbs. lat pulls, the user may present that challenge to a person or group, with 150 lbs and ten repetitions as the goal to beat. Depending on the particular challenge, a time factor might also be applied (e.g., to win the challenge, the repetitions must be completed within a certain amount of time). In other embodiments, a challenge might be presented before exertions take place, with the presenter of the challenge competing in the challenge only after the invitation to the challenge is issued. In some embodiments, the issuer of the challenge (e.g., the first user), can attempt to beat his or her own challenge. For example, if a challenge extends for a period of time and intermittent results reported, a challenge issuer seeing that a competitor already exceeded the threshold, may attempt to beat his or her own threshold.

As shown in FIG. 8, in this exemplary embodiment, input interface 155 may include at least one electronic display device (e.g., touchscreen configured with a tablet device, mobile phone) allowing each jumper to enter personal information. For example, the personal information may include the name, age, gender, contact information. In some embodiments, the personal information may include anatomical data, such as the height and/or weight. The personal information may be stored temporarily in memory 125 and transmitted to database 195.

Figure 9:
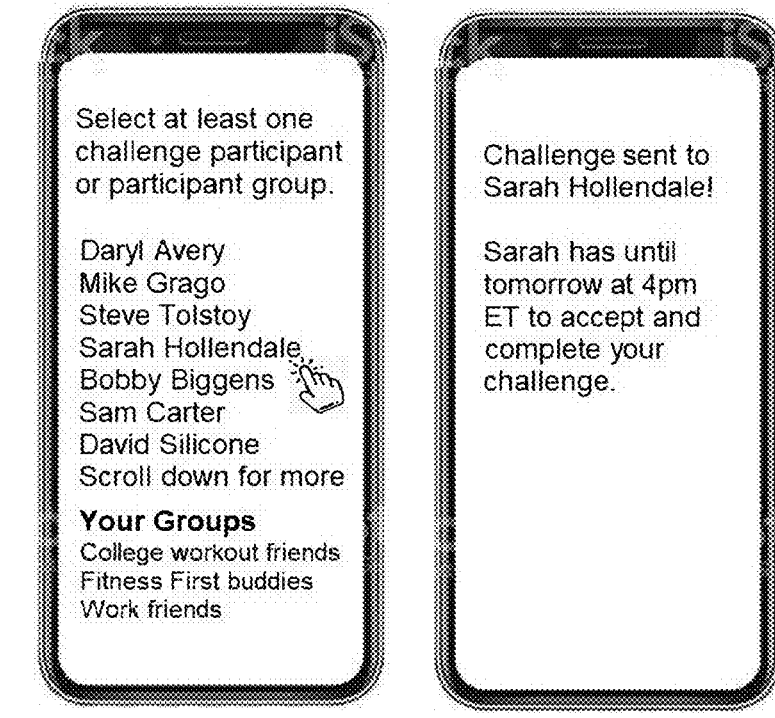
FIG. 9 illustrates three examples of report screenshots consistent with some disclosed embodiments.

FIG. 9 illustrates a series of screenshots exemplifying an input to convert first sensor data into a challenge. After a first user completes a set of repetitions, the user is given an opportunity to convert the sensor data associated with the repetitions into a challenge. In the example of FIG. 9, one or more sensors in the exercise machine (with or without a remote image sensor) determined that the first user performed 15 curls at 60 lbs in 32 seconds. This information was derived from sensors in the machine and may also but not necessarily have been derived from image sensor data from a pared camera to confirm that the first user employed proper form. In FIG. 9, the user is given an opportunity to convert the sensor data into a challenge by clicking "yes" to an associated prompt.

Some embodiments involve receiving a selection of a second subject for receipt of the challenge. A selection of a second subject is a choice of at least one person for receiving the challenge. The selection may be a name or ID of a person or group two or more to whom a challenge is to be sent. Such a selection may occur via a pick list or any other mechanism for designating an individual or a group of individuals. The selection may occur before or after initial exertions are performed For example, a user may configure a system such that all challenges are sent to a particular person or group. Alternatively, at the time of sending a challenge, a user may determine the persons to whom the challenge is to be sent. In some embodiments, the processor may prompt the user initiating the challenge to designate a second user as the second subject to receive the challenge on an input interface. In some embodiments, selection may be performed using a list of available users. A list of available users is stored in a memory in communication with a processor of the exercise equipment. The list of available users may correspond to users of the same exercise equipment or other exercise equipment. The list of available users may be predefined by the initiating user, defined by a server in communication with the exercise equipment or a mobile communications device associated with the initiating user, or a combination thereof. In some embodiments, the processor 112 may subsequently receive a designation or selection of a second subject from user input via one or more input interfaces of the exercise equipment or the mobile communications device.

With reference to FIG. 9, if challenge recipients are not already preselected, receiving a selection of a second subject for receipt of the challenge may occur in response to the first subject being given an opportunity to select a person or group of persons to whom the challenge may be sent. Thus, a pick list may be presented to the first subject, after which the first subject makes a selection of either one person or a group of people. When that selection is made, the selection is said to be received. After making that selection, a message may appear confirming that the challenge was sent. FIG. 9 is but one example of a series of screenshots that may be employed. The actual screenshots and steps involved are a matter of design choice.

In some embodiments, receiving a selection of a second subject for receipt of the challenge includes receiving a selection of a class of subjects, and the second subject is part of the class. The class of subjects may include a group of users who may or may not share a common characteristic. Characteristics of the users may be determined based on, for example, manual input by each user into the exercise equipment or an electronic profile associated with the user, or automatically based on one or more parameters determined based on a user's exercise equipment or mobile communications device. In some embodiments, the class may be defined by at least one of a geographical location, a friends group, or an age group. In some embodiments, the class may be defined based on a physical fitness level or physical ability, such that one class contains users that have been measured by exercise equipment to have a physical fitness level falling within a predefined range of metrics. In some embodiments, the class of subjects may be limited to users that are already known to the initiating user, or may be defined without regard to any preexisting relationship with the initiating user. The one or more processors may, with or without instruction from the user, group certain users into a class from which the second subject is selected.

In some embodiments, when the initiating user designates or selects a class of subject as the receipt of the challenge, one or more processors may or may not add another criteria before sending the invitation. For example, an initiating user may select an entire class of subjects to receive the challenge, without filtering the class to particular users, or selecting one or more specific users. In such embodiments, recipients of the invitation may include an entire class of subjects, group of users, or a subgroup of users. In some embodiments, at least one processor may select a group of user based on stored user-related information. For example, an easy challenge might not be sent to an individual whose fitness level is well above the scope of the challenge, even if the individual might otherwise fall within a selected class. In other embodiments, users might be segregated by class levels depending on past performance. Certain challenges may only be directed to classes corresponding to the difficulty level of the challenge.

Figure 10:
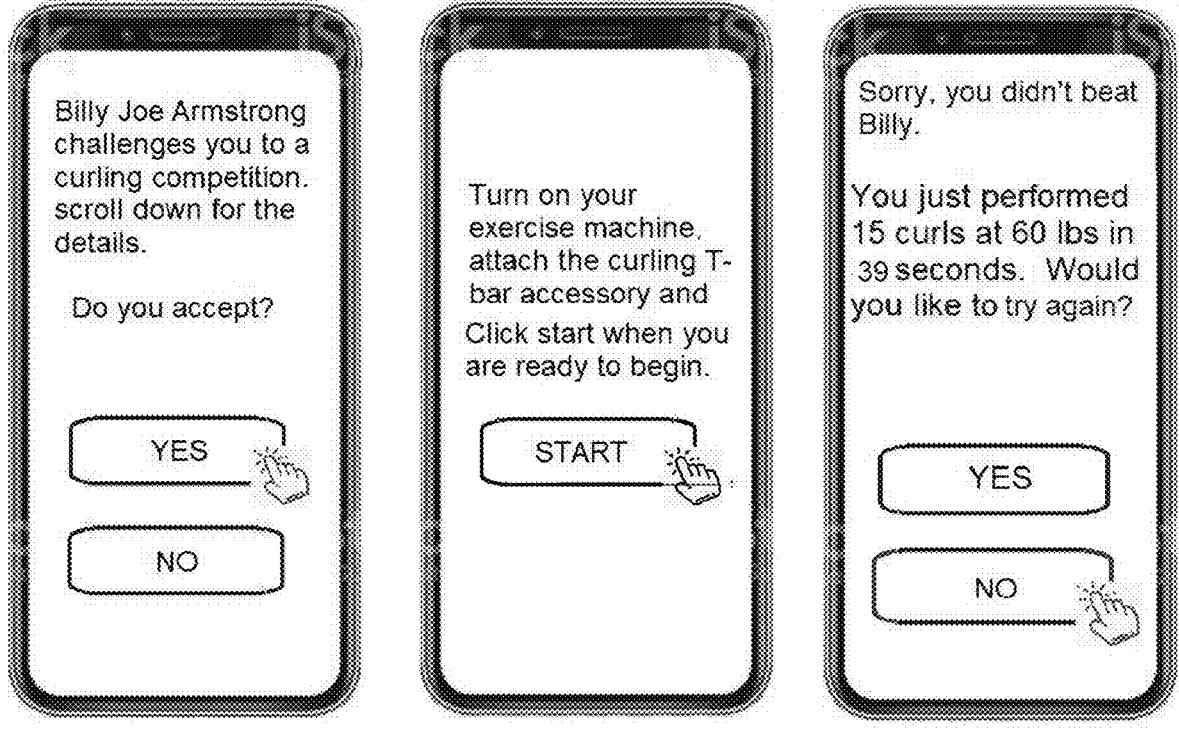
FIG. 10 illustrates two examples of report screenshots consistent with some disclosed embodiments.

Some disclosed embodiments may cause transmission of the challenge to the second subject. Transmission refers to a conveyance of data, messages, or other information from one point in a communication network to another point. In some embodiments, a cloud server may handle one or more aspects of the transmission of the challenge to the second subject. For example, an app associated with the first subject's exercise equipment and/or cell phone may initiate the sending, via a cloud server, of a challenge to one or more individuals. A challenge may show up on the second subject's display as a text message: "Billie Joe Armstrong challenges you to a curling challenge! Do you accept?" Or, you have been challenged to a curling competition, click here to accept," as illustrated in FIG. 10. The transmission of the challenge may include at least one of text, audio, graphics, still images, or video. In some embodiments, the video may include, for example, video of the first exertion by the first subject. The transmission may include data associated with the exertions and first sensor data of the initiating user, so that the exercise equipment associated with the second subject can generate an exercise session associated with the challenge. The second subject user who is the challenge recipient may provide an input to their exercise equipment or mobile communications device with an indication of a choice to accept or decline the challenge. Furthermore, a designation or selection of additional subjects for receipt of the challenge may be received by one or more processors, and the one or more processors may cause transmission of the challenge to the additional subjects. Such additional subjects could be from a same group or multiple groups. For example, if multiple challenge recipients are selected in FIG. 9, then a host server will receive an identification of multiple individuals, and will send the challenge of FIG. 10 to devices of those additional individuals.

In some embodiments, if a second subject, such as the user of the challenge recipient, accepts the challenge, an electronic acceptance of the challenge may be received from the second subject. Electronic acceptance includes data or information associated with the second subject agreeing to perform the challenge exertion. In some embodiments, the electronic acceptance may be a binary signal such as a field with a "1" or "0" indicating that the second subject has accepted the exertion challenge. In some embodiments, the acceptance may include further information such as at least one of text, audio, graphics, still images, or video received from one or more devices associated with the second subject(s) or the cloud server. In some embodiments, the video may include video data from the challenge recipient.

FIG. 10 Illustrates an example of a user interface enabling a user to accept a challenge. In a first series of screen shots, the challenge is presented and the user is asked to accept. If the user accepts, a signal (i.e., an electronic acceptance) is sent to a processor. Upon receipt of the electronic acceptance, the processor identifies the sender as participating in the challenge. As previously mentioned, the receiving processor may constitute or be part of a server that mediates the challenge.

The acceptor of the challenge may they be prompted to begin the challenge. The prompt may be a request to initiate an exertion or set of exertions, and may include information about how to perform the exertion. For example, a video of proper performance of the exertion may be displayed, or graphic images depicting the exertion may be displayed. While a user may click a start button, as another alternative, voice recognition may note the beginning of an exertion through detection of a stated word or words, such as "start now." Alternatively, once start is selected, a timer may not begin running until an initiation of an exertion is detected by one or more of the sensors described herein.

In some embodiments, an electronic acceptance of the challenge may include second sensor data reflecting a second subject performing a second exertion. As an alternative to an acceptance such as the "Yes" click illustrated in FIG. 10, performance of the challenge may constitute an acceptance. That is, if the challenge recipient performs the challenge activities within a prescribed period such as a challenge time frame or a period of time after receipt of the challenge, that performance may be recognized as an acceptance. The second sensor and second sensor data may be similar in type and nature to the first sensor and first sensor data. In some embodiments, as the second subject performs a second exertion to participate in the challenge, one or more processors may capture second sensor data reflecting the second subject performing a second exertion via a second sensor. In some embodiments, the second exertion may be, similar to the first exertion, and associated with one or more sensors. In some embodiments, the second sensor could be integrated into one or more components of a second exercise equipment such as sensors of a resistance motor 140 in FIGS. 12A, 12B, and 12C. In some embodiments, the second sensor may include one or more image sensors attached to the exercise equipment or in communication with one or more processors, such as in the examples illustrated in FIGS. 12A, 12B, and 12C.

In some embodiments, the second exertion may, similar to the first exertion, include a series of exertion repetitions. The second exertion may be the same as, or directly comparable to, the first exertion. The series of exertion repetitions may have a quantity equal to those of the first exertion, or may be greater than or fewer than the first exertion by the initiating user.

In some embodiments, the second sensor data. like the first sensor data, may include outputs of one or more resistive motors. In some embodiments, the second sensor data may be from at least one sensor measuring at least one characteristic of the resistive motor 140, for example, an amplitude, a frequency, a phase, a timing (e.g., on/off), a direction, and/or any other characteristic of an electrical and/or an electromagnetic signal. In some embodiments, the second sensor data may correspond to motions of the cable 206, and include at least two of cable length pulled, cable velocity, a time interval between cable pulls, and an overall duration of the second set of exertions performed by the second subject. The second sensor data and associated sensors may be similar to those of the first sensor data.

In some embodiments, the second sensor data, further includes an output of an associated image sensors, similar to the first sensor data. In some embodiments, one or more image sensors may be associated with a camera system in communication with one or more processors of the exercise equipment or a mobile communications device in communication with the one or more processors. The one or more image sensors may provide image data to one or more communication links such as transmitters capable of transmitting captured images to one or more processors (e.g., processor 112 or a different processor) for image processing. Such associated image sensors may be consistent with the examples illustrated in FIGS. 12A, 12B, and 12C.

In some embodiments, this exemplary embodiment, output interface 145 may include at least one electronic display device. In some embodiments, output interface 145 includes a first electronic display device for presenting real-time feedback to a jumper during the jumping challenge, and a second electronic display device presenting a leaderboard comparing the performance, e.g., of a single jumper performing different jumps or of multiple different jumpers that have participated in the jumping challenge. In some embodiments, the same electronic display device may present real-time feedback to the jumper as well as the leaderboard presenting the scores of jumpers who completed the jumping challenge). The term "leaderboard" may refer to a presented or published list ranking competing individuals performing a common task according to their relative success with respect to the other competing individuals. The relative success may be based on one or more criterion, such as speed, accuracy, distance covered, cooperation with other individuals, or any other criterion related to the common task. The leaderboard may help the competing individuals assess their relative success and motivate them to improve their performance. The leaderboard may be updated in real-time throughout the jumping challenge.

In some embodiments, input interface 155 and output interface 145 use the same electronic display device. Some embodiments may include multiple output interfaces. For example, a user may view information retrieved from the database related to the jumping challenge on his mobile phone and/or via an electronic screen of a tablet device, such as the tablet device used to enter the jumper's personal information.

In some embodiments, the second sensor data may reflect a degree of completion of the second exertion and/or a quality of the second exertion, comparable to how the first sensor data reflected a degree of completion of the first exertion. In some embodiments, the second sensor data and the first sensor data may be directly comparable because they are measurements of the same parameters. In some embodiments, a comparison of the first sensor data and the second sensor data may provide an assessment result of which indicates a better quality completion or execution of the exertion, discussed in further detail below.

In some embodiments an electronic comparison of the first sensor data and the second sensor data may be used to confirm that the second exertion complies with the at least one parameter. Confirming compliance involves determining that the first sensor data and the second sensor data conform to a rule, command, expectation, guidelines, requirements, and any other measurable metrics for confirming that the first and second sensor data is suitable for evaluating the exertion challenge. At least one parameter includes at least one characteristic common to the first and second exertions. For example, in a challenge involve bicep curls, a parameter might be that the length of cable pull must exceed 0.75 m. Or the parameter might be associated with the biology of each individual participant. A shorter individual with shorter arms might be able to complete a full bicep curl in 0.6 m. In some embodiments, compliance with a parameter might take into account the biology of each participant. Another example of a parameter is form. Machine vision might be applied to an image sensor output to confirm that a participant complies with certain form requirements for the exertion. If the exertion involves jumping, a form requirement might be that the participant jumps by a certain amount. If the form requirement involves an exercise where the back should be kept straight, image analysis may confirm that each repetition complied with the straightness threshold. In some embodiments the comparison may only involve one two parameters. In other embodiments, 3,4, 5, 6 or more parameters might be compared.

In some embodiments, one or more processors of a cloud server, of the first or second exercise equipment, or of one or more mobile communications devices, may confirm that the collected second sensor data is of a similar type or format as the first sensor data, such that a comparison of the two sensor data sets can be made. Thus, one or processors may verify both the first and the second sensor data reflect compliance with the at least one parameter.

In some embodiments, in order to perform an electronic comparison of the first sensor data with the second sensor data to confirm compliance, one or more processors may perform various steps including preprocessing, alignment, feature extraction, running one or more comparison algorithms or rules, making decisions of discrepancies between the two data sets, and/or providing an output. For example, one or more processors may perform preprocessing by cleaning, filtering, normalizing, or transforming the data to a suitable format for further analysis and comparison with the other data set. The one or more processors may align the data by determining whether the first and second data are synchronized or sampled at a same rate, and if not, then may align the data sets along one or more scales such as time. Such alignment may ensure that the first and second data sets for the same exercise movements and/or same repetitions are accurately compared from both the first and second sensors. In some embodiments, relevant features or characteristics may be extracted from the first and second sensor data sets, such as specific values in the data sets, one or more statistical values of the data sets, or patterns representing information pertinent to the challenge. The one or more processors may then apply one or more rule sets or comparison algorithms to assess a similarity or dissimilarity between extracted features from the first and second sensor data. Such comparison may involve, for example, machine-learning based techniques, a correlation analysis, or distance metrics between the first and second aligned data sets. Based on the comparison, the one or more processors may determine discrepancies between the first and second sensor data sets and provide an output indicating whether the first and second exertion comply with the at least one parameter.

If a comparison determines that the second subject is not a leader, and the challenge is still active, a prompt may be provided in one embodiment, as illustrated in FIG. 10 to try again. If the second subject desires, the second subject may try again. Similarly, if the second subject becomes the leader and the challenge is still active, the first subject may receive a message notifying that the second subject has taken the lead and prompting the first subject to try again. In this way, multiple remote participants may motivate each other's performance.

In some embodiments, when the electronic comparison confirms that the second exertion complies with the at least one parameter of the first exertion, metrics of the first sensor data and the second sensor data may be compared to determine a challenge dominator. A challenge dominator is an individual who is either in the lead or who has won the challenge. In a one-on-one challenge, the least one processor may compare the first and second sensor data sets directly. In some embodiments, when there are multiple second subjects, there could be multiple sets of second sensor data, such as a data set for each challenger subject. In such instances, all the second data sets are compared by at least one processor, either one at time or using any methodology to determine a dominator. The one or more processors may determine a challenge dominator as the user who achieved the highest levels of metrics in the sensor data associated with one or more rules for identifying a dominator. The dominator may be associated with a particular combination of metrics in their respective sensor data, such as a maximum number of repetitions performed within a predetermined time frame, or a maximum number of repetitions performed at or above a minimum resistance level. In some embodiments, the metrics may be pieces of the sensor data, or may be information derived using the sensor data, such as a volume of "weight" determined by multiplying a number of repetitions by a level of force that is calibrated to be a simulation of lifting a certain amount of weight. The foregoing are examples to provide a general understand of inventive principles and it is to be understood that the types and/or combinations of metrics used for comparing sensor data to determine a dominator of the challenge are not limited to the disclosed examples.

More particularly, one or more processor, such as processor 112, may determine characteristics to be used as the metrics of the first and second sensor data to determine the challenge dominator. Because the first sensor data and the second sensor data may each include at least one characteristic, the one or more processors may compare sensor data and determine a common characteristic, or multiple common characteristics. In some embodiments, the one or more processors may consider the implications of the common characteristics and decide whether they may provide substantial substantiation as the challenge dominator. In some embodiments, the one or more processors may choose one or more characteristics as the challenge dominator when these characteristics effectively imply the quality of the exertion done by the subject. In some embodiments, some common characteristics are not capable to distinguish the quality of the exertion. The one or more processors may not choose them as the challenge dominator.

Some disclosed embodiments involve outputting a report to the first subject and the second subject identifying the challenge dominator. A report may include any form of notification. It may include a message in an app, an email, a file, or any other form of information reporting one or more results of a challenge. The report may be output by a cloud server after comparing results or may be output by an endpoint, such as a mobile communications device of one of the participants. A single report may be provided at the end of a competition, or intermediate results, such as a leader board or personal standings may be provided while the competition is ongoing.

In some embodiments, comparing the metrics and outputting the report occurs on a server remote from the first subject and the second subject. A server as described elsewhere herein may serve as an intermediary in the competition and may send a report, or differing forms of the report to challenge participants. The server may be a remote physical server, a virtual server, a cloud server, or a computing architecture including a combination thereof. In some embodiments, one or more processors may perform the comparison of the metrics and the outputting of the report on a cloud-based server.

In some embodiments, at least one report may take the form of a leader board. A leader board may be a table or ranking list indicating relative rankings or scores of the initiator user and the second subject(s). In some embodiments, the leader board may display one or more other users who completed the same challenge, even if they were not engaged by the initiating user. The leader board may provide a static or dynamic visual interface to track and compare the performance or achievements of users.

In some embodiments, the report may at least include an indication of the dominator and/or an award for the dominator. The award may include virtual tokens such as stars or dumbbells. The amount of the award may be dependent, for example, on the difficulty of the challenge or the number of individual who participated. For example, five credits may be awarded for a challenge involving five participants, and 100 credits may be awarded for a challenge involving 100 participants. In this way, group participation may be encouraged. In some embodiments, the report may identify the first subject and the second subject. In some embodiments, the report may provide an interpretation of at least a part of the first sensor data and the second sensor data (such as an interpretation of the subjects' performances based on their respective sensor data.) Thus, the leader board may list users who performed the challenge and yielded metrics associated with the dominator at the top position or positions, and may display users descending in order from the best-performing to worst-performing. Such an order may be determined based on the comparison(s) of sensor data to metrics disclosed herein.

FIG. 11 depicts two forms of a common report, notifying both the dominator and the unsuccessful participant of the outcome of the challenge. In some embodiments, the report may only notify of whether a subject has won or lost. In other embodiments, the margin of win or loss may be reported, such as illustrated in FIG. 11. In yet other embodiments, a final leader board may constitute at least a part of the report.

Some disclosed embodiments involve notifying the second subject of a time-period for receipt of the second sensor data and terminate the challenge when the second sensor data is not received during the time-period. The time period for receipt refers to when a challenge ends. For example, at the time a challenge is sent or at some other time, the second subject(s) may be notified of either a duration of the challenge or a date and time when the challenge expires. Once the time of expiration passes, the challenge is closed. If a leader board is provided, it may be updated until the expiration of the challenge. The user (e.g., the first subject, or the one initiating the challenge) may decide the time-period (or ending), or it may be predetermined or calculated by the one or more processors. The time-period may extend for minutes, hours, or days, depending on preference, from a time of receipt of the first data. For example, the time-period may extend a certain amount of time (such as minutes, hours, days, weeks) from the initiation or acceptance of the challenge. In some embodiments, the time-period may extend to a deadline such as a particular date and/or time.

In some embodiments, prior to expiration of the time-period, if the challenge is not responded to by the second subject, a reminder may be provided in the form of a notification to the second subject that there is a pending challenge from the first subject. Thus, prior to expiration of the time-period, one or more processors may notify the second subject that the first subject is dominant, and may then enable the second subject to make at least one additional challenge attempt. In some embodiments, the second subject may have multiple challenge attempts and the one or more processors may select of the best of the multiple challenge attempts for a particular subject. Referring now to FIG. 13, a block diagram of an exemplary method for asynchronous user initiated and cloud mediated exertion challenge operations. In some embodiments, code with instructions for causing one or more processors to perform operations set forth in the steps in FIG. 13 may be stored in a non-transitory computer readable medium. Operations may be performed based on instructions executed by, for example, at least one processor such as processor 112. In step S1310, a processor such as processor 112 may capture, via at least a first sensor, first sensor data reflecting a first subject performing a first exertion, consistent with the examples discussed above.

In step S1320, one or more processors may receive an input to convert the first sensor data into a challenge, consistent with some disclosed embodiments as described earlier. For example, as illustrated in the far left user interface of FIG. 10, a user interface such as on a mobile communications device may provide an interactive interface for allowing a user to provide an input to convert first sensor data for a first exertion into an exertion challenge.

In step S1330, one or more processors such as processor 112 may receive a selection of a second subject for receipt of the challenge, consistent with some disclosed embodiments. For example, as illustrated in the center user interface of FIG. 9, a user interface such as a mobile communications device interface may provide an interactive list of second subjects, for receiving an input from the user selecting second subject(s) for receipt of the exertion challenge.

In step S1340, a processor such as processor 112 may cause transmission of the challenge to the second subject, consistent with the examples discussed above. As illustrated in the right user interface of FIG. 10, a user interface such as a mobile communications device interface may provide a confirmation that the exertion challenge was sent to the second subject. In some embodiments, one or more user interfaces may also indicate a time limit for the second subject to accept and complete the exertion challenge, discussed in further detail below.

In step S1350 an electronic acceptance of the challenge is received. Such receipt occurs on a processor, as described earlier.

In step S1360, a processor captures second sensor data reflecting the second subject performing a second exertion via a second sensor, as described earlier.

In step S1370, a processor such as processor 112 may confirm via an electronic comparison of the first sensor data and the second sensor data that the second exertion complies with at least one parameter, as described earlier.

In step S1380, when the electronic comparison confirms that the second exertion complies with the at least one parameter of the first exertion, the metrics of the first sensor data and the second sensor data are compared to determine a challenge dominator. It is important to note that comparing metrics does not necessarily require the precise sensor outputs to be determined. Rather, indications or derivatives of the sensor data may be compared. In this way, a dominator is determined.

In step S1390, a report is output to the first subject and the second subject identifying the challenge dominator. The report may be the same for both the first subject and the second subject, or the report may have different forms for the different subjects, as illustrated in FIG. 11, and as described elsewhere herein.

Figure 3B:
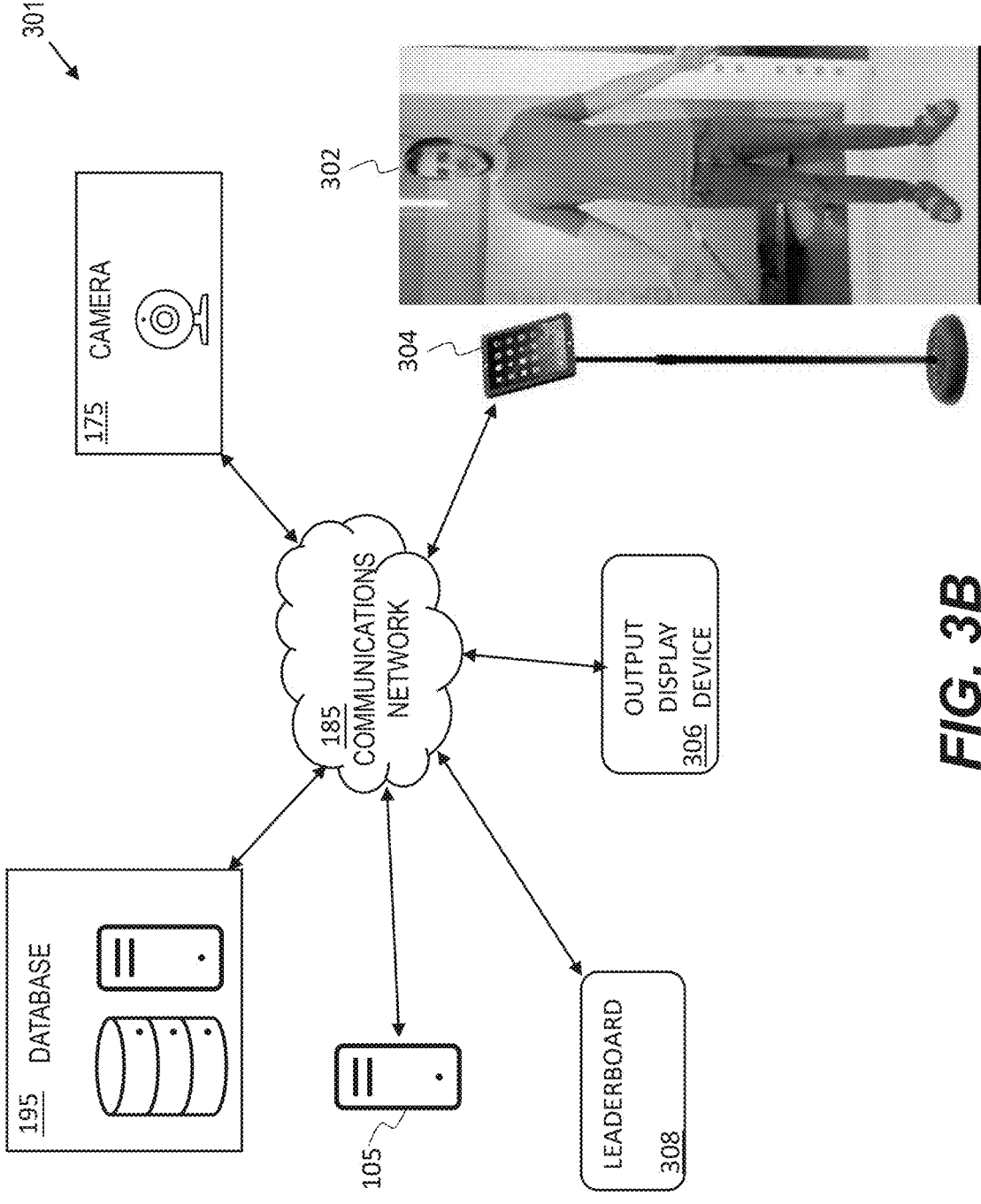
FIG. 3B is a schematic diagram of an exemplary use case for a jumper participating in a jumping challenge.

FIG. 3B shows an exemplary use-case 301 for a jumper 302 participating in a jumping challenge using one or more components of CV jump competition system 103 (see FIG. 8), consistent with disclosed embodiments. Use-case 301 may include a tablet device 304 corresponding to input interface 145, and an output display device 306 and a leaderboard 308 corresponding to output interface 155. In some embodiments, tablet device 304 may be used in place of or in addition to an exercise machine 200 having a camera 175 or a mobile communications device 224 camera that is paired with an exercise machine 200, consistent with disclosed embodiments. To enter a jumping challenge, jumper 302 may enter his personal information (e.g., at least a name and contact information) into a tablet device 304. Computing device 105 may store the personal information in database 195 using communications network 185. Camera 175 may acquire one or more images of jumper 302 and provide the one or more images to CV engine 115 of computing device 105. In some embodiments, tablet device 304 and computing device 105 may be the same device.

CV engine 115 may receive the one or more images of jumper 302 and analyze the one or more images to trace an outline of the body of jumper 302 and determine multiple key points for jumper 302, such as corresponding to the skeletal joints of jumper 302 (e.g., one of more of the feet, ankles, knees, hips, elbows, wrists, neck, shoulders, or any other point for tracking a jumping motion of jumper 302). CV engine 115 may create a skeletal mapping for jumper 302 from the plurality of key points. The physiological indicators for jumper 302 may be stored in memory, such as memory 125 and/or database 195. In some embodiments, camera 175 is a 3D camera and CV engine 115 may perform a 3D scan of jumper 302 based on the at least one image, for example to generate a 3D model of jumper 302.

In some embodiments, the CV engine may receive an image from the camera at a frequency ranging from 30 to 60 Hz. The CV engine may create a point for each image received. Each data point may include a time stamp, 2D and 3D locations on the body of the jumper for each key point, the current body distance from the surface, the last jump height, the number of jumps jumped thus far by the jumper. CV engine may provide this data to the computing device in real time. In some embodiments, the computing device may notify the CV engine when to begin and when to cease tracking the motion of the jumper.

In some embodiments, the CV engine may run on a dedicated computer or on a side board computer, or a single board computer.

Turning to FIG. 4, illustrations of an exemplary 3D model 400 and an exemplary skeletal map of key points 402 for jumper 302 (FIG. 3B) are shown. CV engine 115 may generate 3D model 400 and skeletal map 402 from one or more images 404 of jumper 302 received from camera 175. In some embodiments image 404 is a 3D image of jumper 302.

After the personal information has been received and the key points of a jumper (e.g., jumper 302) have been mapped, the jumper may begin the jumping challenge. In some embodiments, the jumper may be required to stand in a predefined area during the jumping challenge. For example, the predefined area may be within a specific optical detection range of camera 175, at a predefined distance of a backboard presenting various heights (e.g., as notches), or any other positioning requirement of the jumping game.

In some embodiments the jumping challenge may be initiating by starting a timer, e.g., configured with computing device 105. For example, the timer may be set manually, in response to computing device 105 detecting a jumper performing a jump, via a voice command (e.g., "Start"), or any other method for starting the jumping challenge. The timer may measure a predefined time period for the jumping challenge (e.g., as a timed competition). For example, the jumping challenge may be defined by the number of qualifying jumps a jumper can perform in 20 seconds (e.g., above a threshold, for example 10 cm or 15 cm), or the highest jump performed within the time period, or the fastest series of qualifying jumps performed in given time span within the time period, or any other criterion defining the jumping challenge. The motion of the jumper during the time period measured by the timer may be captured by camera 175 and provided to CV engine 115, e.g., via communications network 185.

CV engine 115 may assess in real-time qualitative and/or quantitative parameters associated with the jumps performed by the jumper, such as by tracking the movements of the jumper and making one or more decisions relating to assessing what movements are jumps, which jumps are qualifying jumps, and characteristics of each jump, such as the speed, the frequency of multiple jumps, the maximum height reached, the average height reached the cumulative height reached, the form (e.g., poise, balance and/or position accuracy on landing), and any other criterion relevant to the jumping challenge.

For example, if the camera includes a 3D depth camera, each pixel of an acquired image may include the distance from the camera. The CV engine may trace an outline of the body of the jumper using the 3D images and measure the distance between each key point and the surface. The minimum distance may be the current height of the jumper from the surface. If the body remains substantially rigid, the distance may be based on the center of mass. If the body does not remain rigid (e.g., the jumper bends or twists), the outline of the body may be used to find the minimum point on the outline to the surface.

As another example, if the camera is a 2D camera, the distance may be based the laws of gravity, for example by measuring the time it takes for the body of the jumper to fall to the surface from an airborne start velocity of zero. on time of falling and gravity. As another example, the 2D camera may be calibrated such that the direction that the camera is focused on may be known for each pixel, and the distance between the camera and the jumper may be known. Based on this information, the CV engine may determine the height of the jumper, and from the change in angles during each jump, the CV engine may determine the height of each jump.

As another example, if the camera has a limited view, a board may be positioned behind the jumper, with notches or marks indicating various heights.

Computing device 105 may receive information from CV engine 115 related to the jumping challenge in real-time, including the qualitative and/or quantitative assessments associated with the jumps performed by the jumper. For example, CV engine 115 may use image processing and/or motion detection techniques to determine a jump and the maximum height attained during the jump. Computing device 105 may use the information to provide real-time feedback to the jumper during the jumping challenge, for example by displaying via output display device 306. For example, computing device 105 may display the time remaining for the jumping challenge, the current distance of at least one key point of the jumper relative to the surface (e.g., using the surface plan) in real-time, whether or not a jump is a qualifying jump, the number of qualifying jumps performed thus far, the maximum height reached by the jumper, and additional feedback relating to the speed, form, balance, agility, flexibility, or any other indicator relevant to the jumping challenge. In some embodiment, output interface 155 may include a speaker for issuing feedback, such as a bell ring when a jump is determined to be a qualifying jump, or when a height record is broken.

Figures 5A, 5B, 5C, 5D, 5E, 5F:
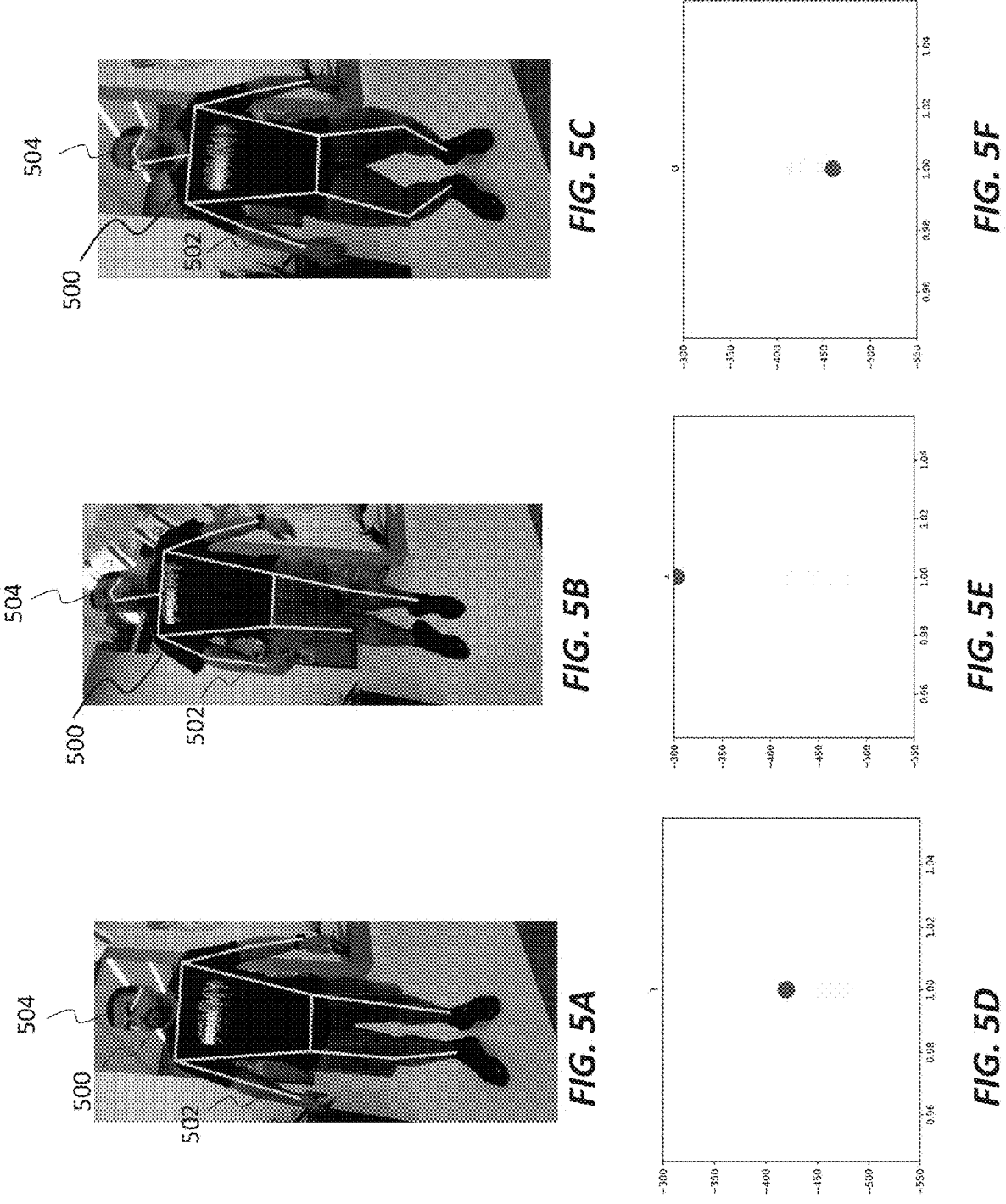
FIGS. 5A-5G are illustrations of an exemplary jumping challenge, consistent with some disclosed embodiments.
Figure 5G:
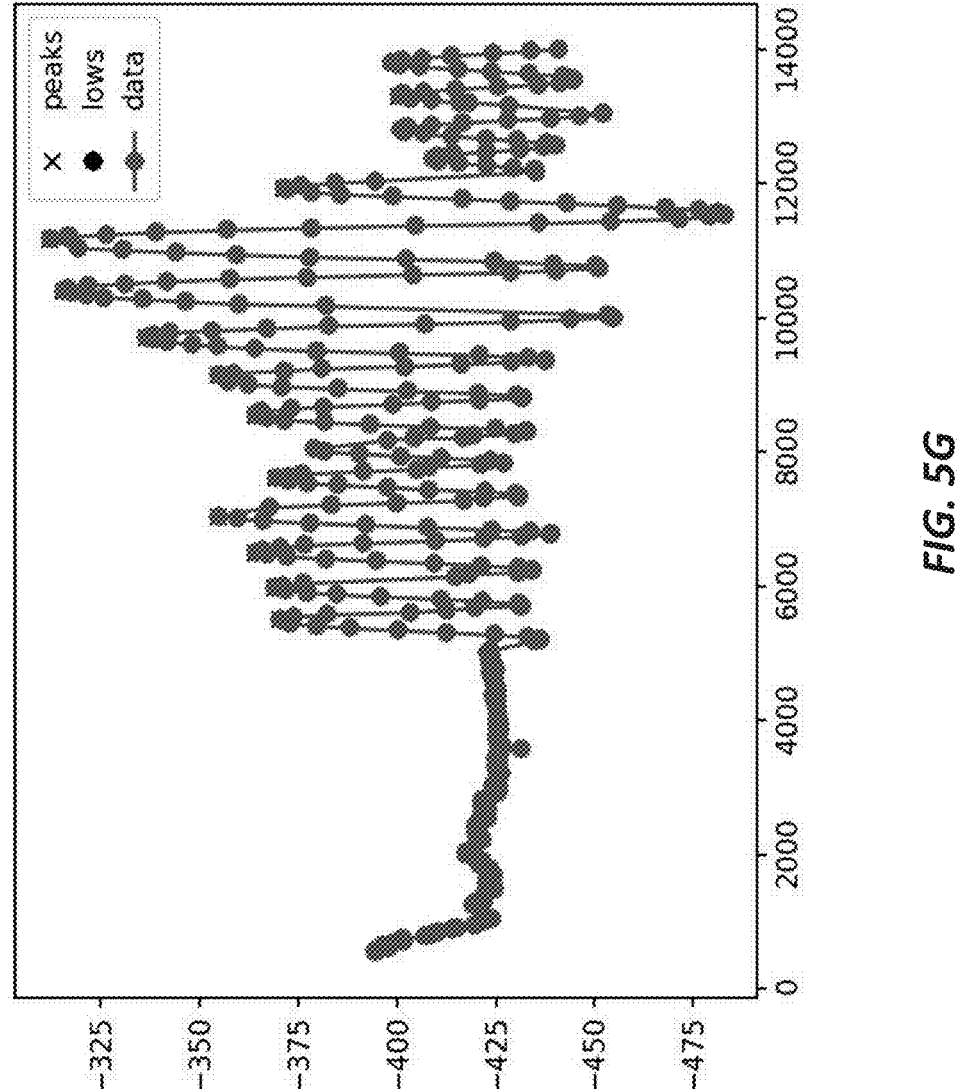

Turning to FIGS. 5A-5G, an exemplary implementation of a jumping challenge is shown. FIGS. 5A-5C illustrate images of a jumper 500 participating in a jumping challenge with an overlaid skeletal map 502 of key points determined by a CV engine (e.g., CV engine 115 of FIG. 8). FIGS. 5D-5F, corresponding to FIGS. 5A-5C, respectively, illustrate the height achieved by jumper 500 determined by the CV engine, indicated as a dot on a plotted on a height graph. For example, CV engine may track the head 504 of jumper 500, for example to correct for jumper 500 bending his knees, twisting his back, or pointing his toes during the jumping challenge. Accordingly, in FIG. 5A, jumper 500 is standing on the surface (e.g., floor) in a substantially upright pose, and the height between head 504 and the surface is 420 (FIG. 5D). In FIG. 5B, jumper is air-born and the height of head 504 to the surface is indicated as 300 (FIG. 5E). In FIG. 5C, jumper 500 is bending his knees, lowering his head 504, such that the height is 460 (FIG. 5F). Turning to FIG. 5G, a graph is shown plotting the height of head 504 of jumper 500, over time throughout the jumping challenge. While the Figures illustrate determining the jumping height according to the head of the jumper, other criterion may be used, such as the height of the feet, the knees, center-of-mass (e.g., approximated by the hips), shoulders, or any other anatomical part of the jumper.

Figure 6A:
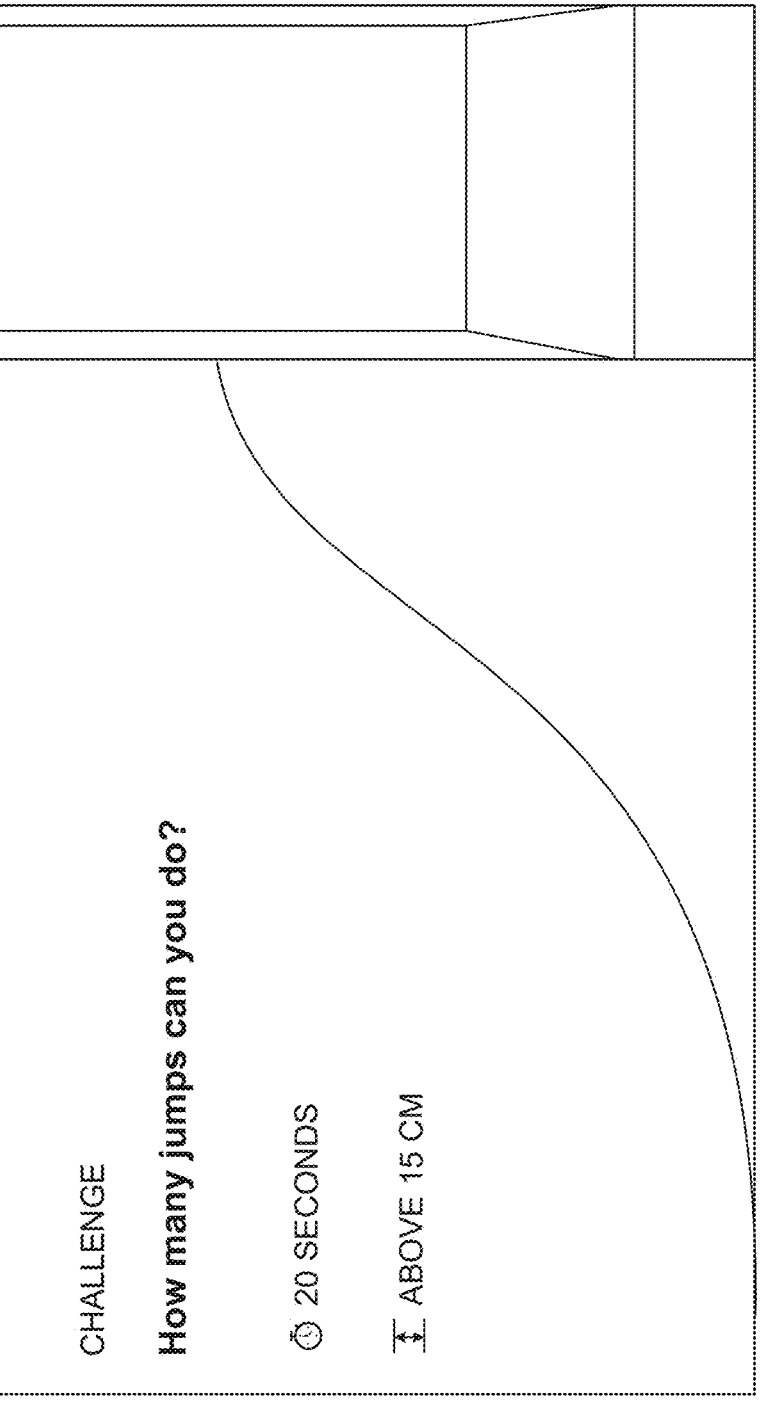
Figure 6B:
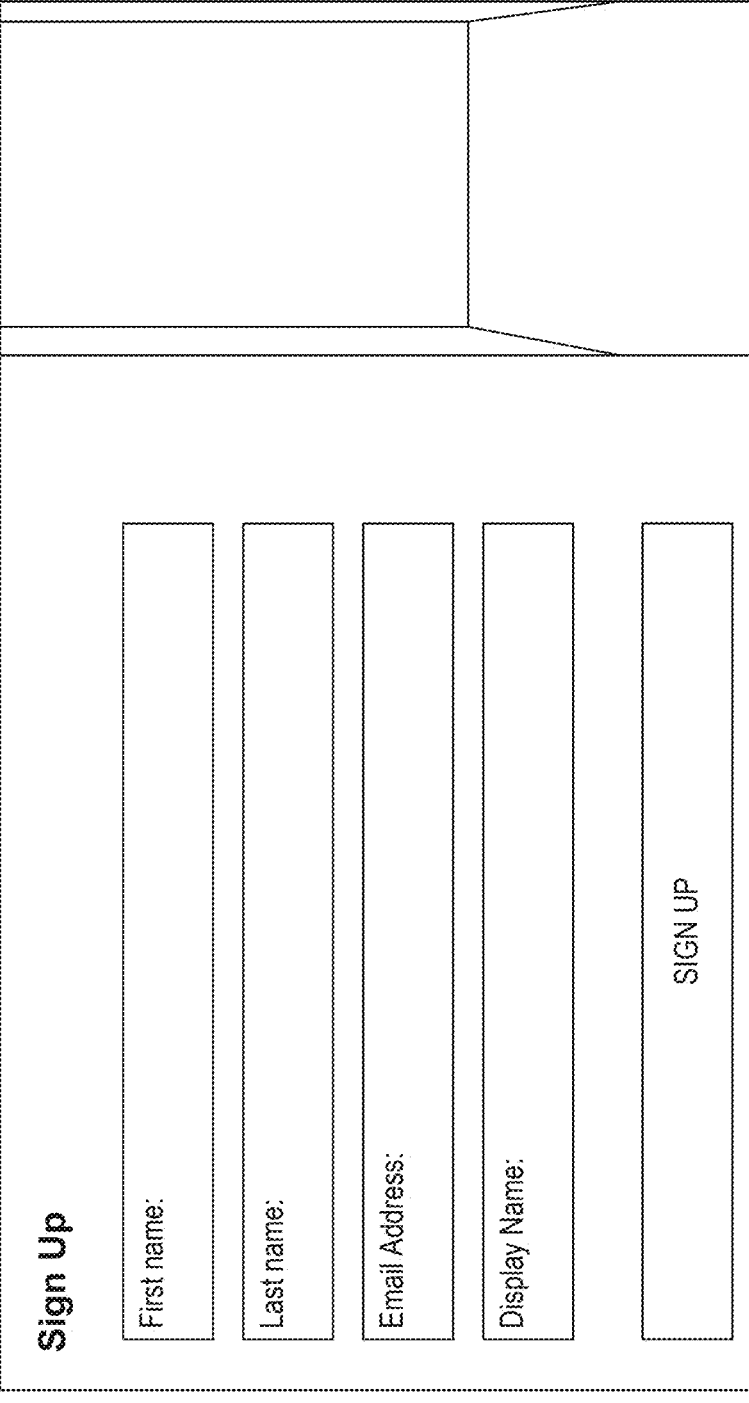
Figure 6C:
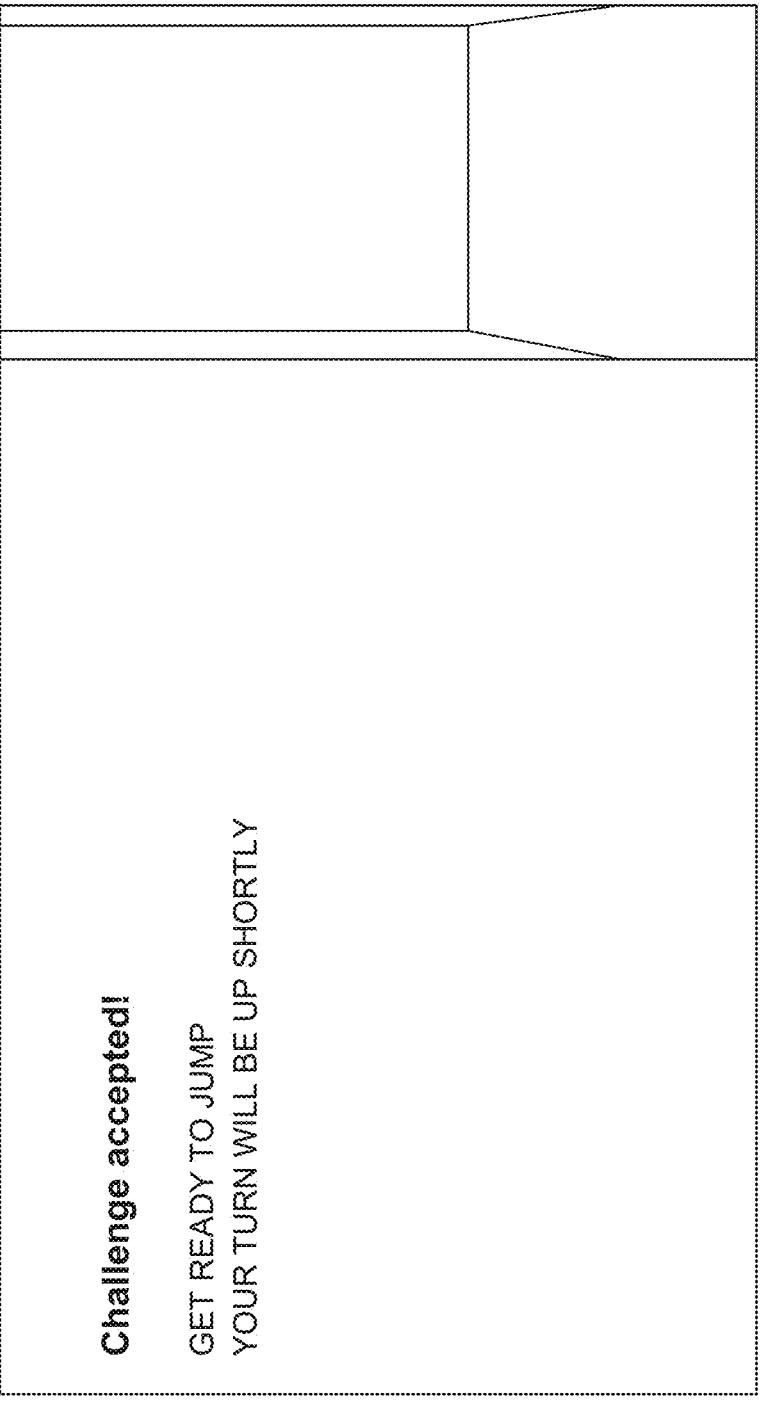
Figure 6D:
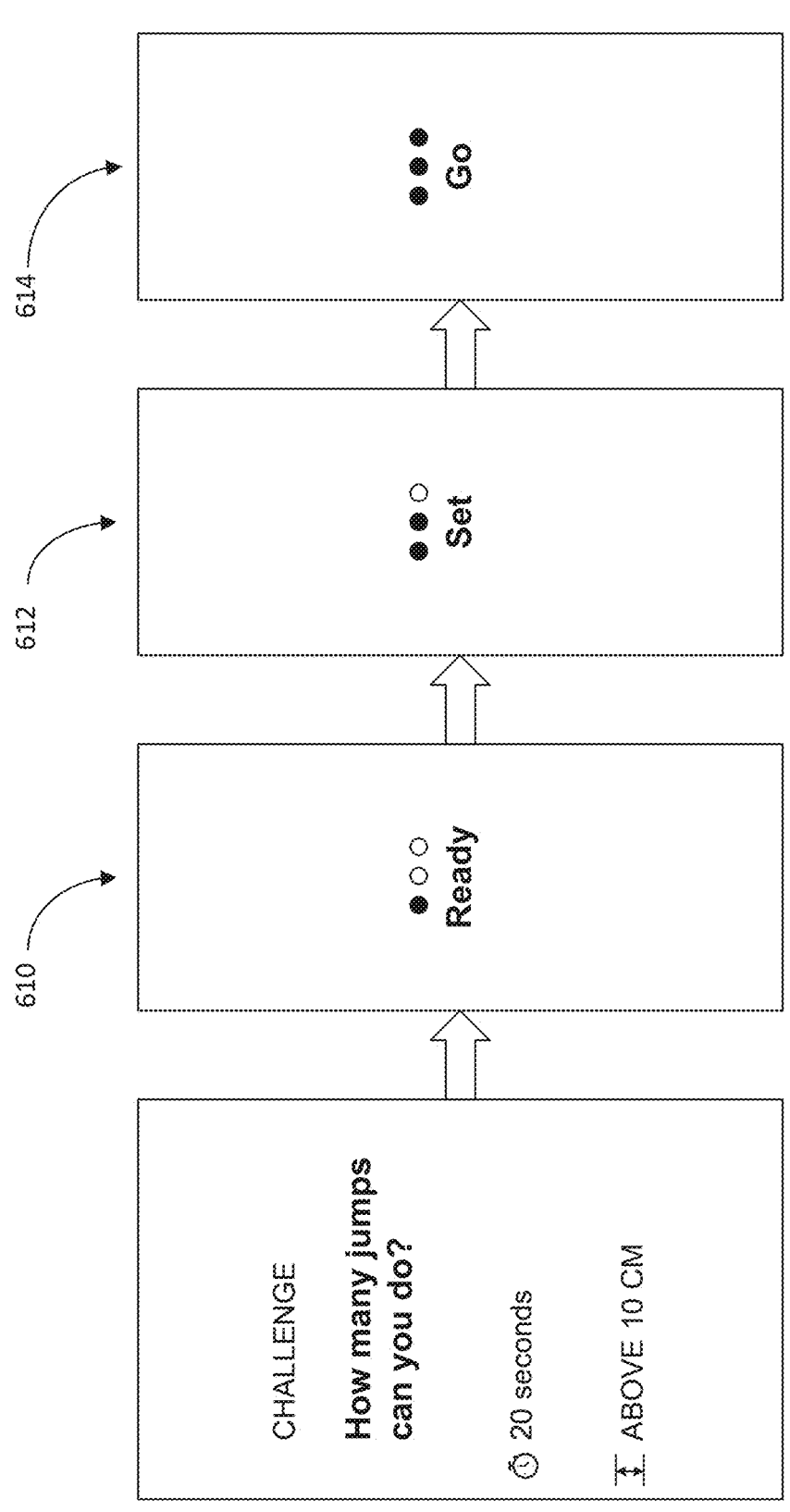

Referring to FIGS. 6A-6K, user interfaces associated with another exemplary implementation of a jumping challenge are shown. FIG. 6A illustrates a welcome screen for a jumper wishing to participate in a jumping challenge. For example, this particular competition is defined as how many jumps above 15 cm a jumper can perform in 20 seconds. FIG. 6B illustrates a user interface (e.g., input interface 145) allowing a jumper to enter personal information, such as a name and contact information before beginning the jumping challenge. The information may be stored in a database tracking the performance of the jumpers participating in the competition. FIG. 6C illustrates a confirmation via a display screen (e.g., output interface 155) that the jumper may begin the jumping challenge. FIG. 6D illustrates three successive screens, 610, 612, and 614, prompting the jumper to begin the jumping challenge.

Figure 6E:
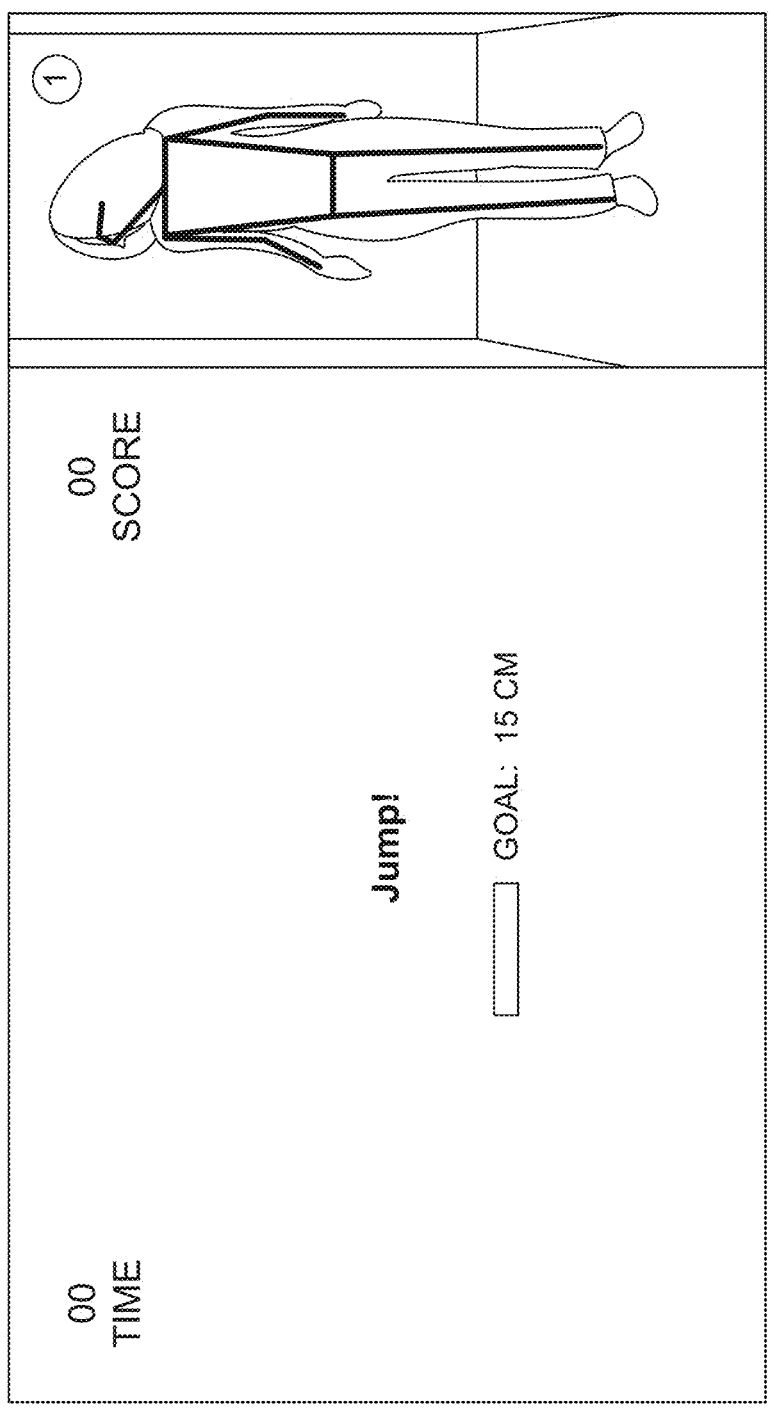
Figure 6F:
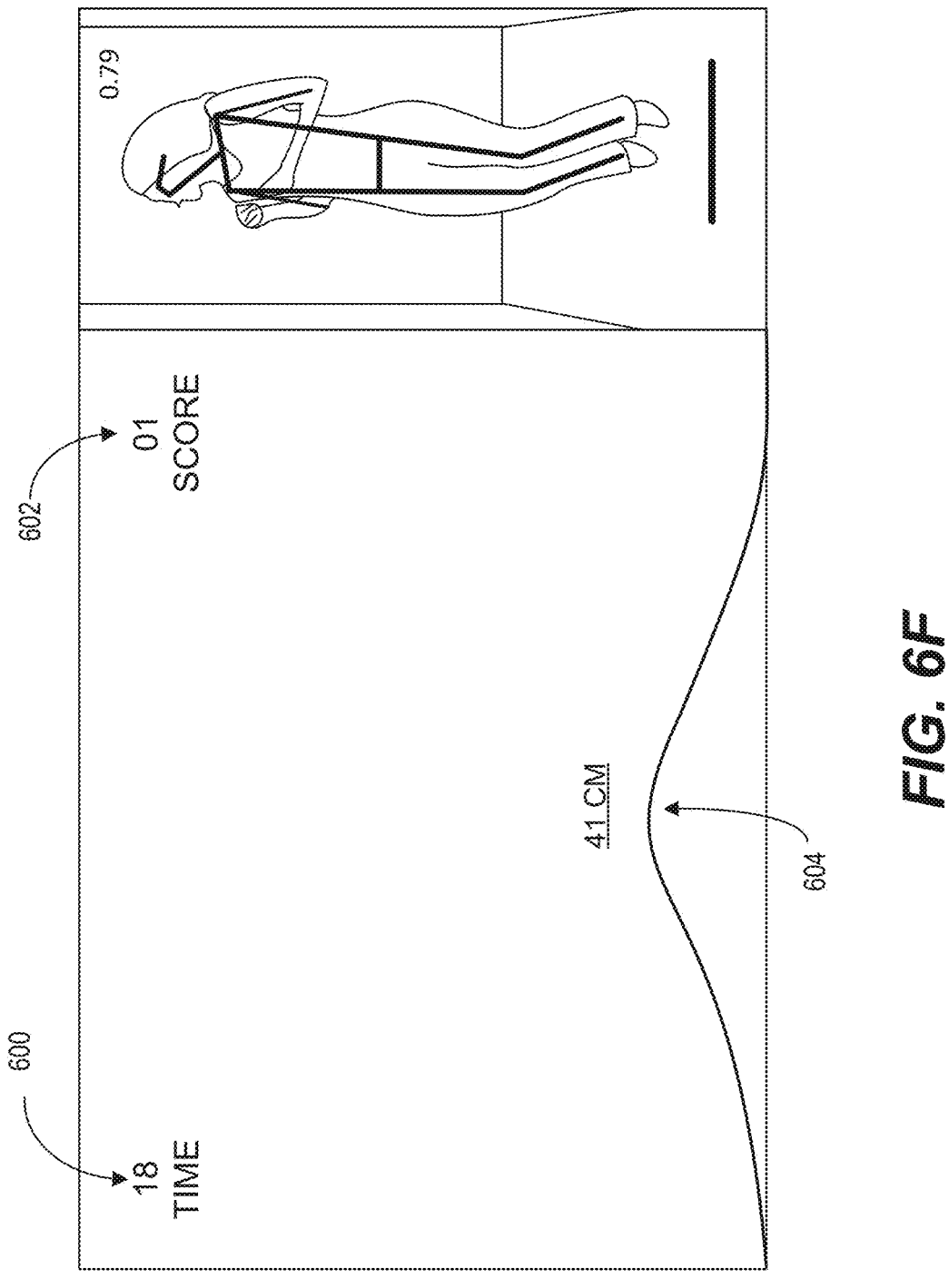
Figure 6G:
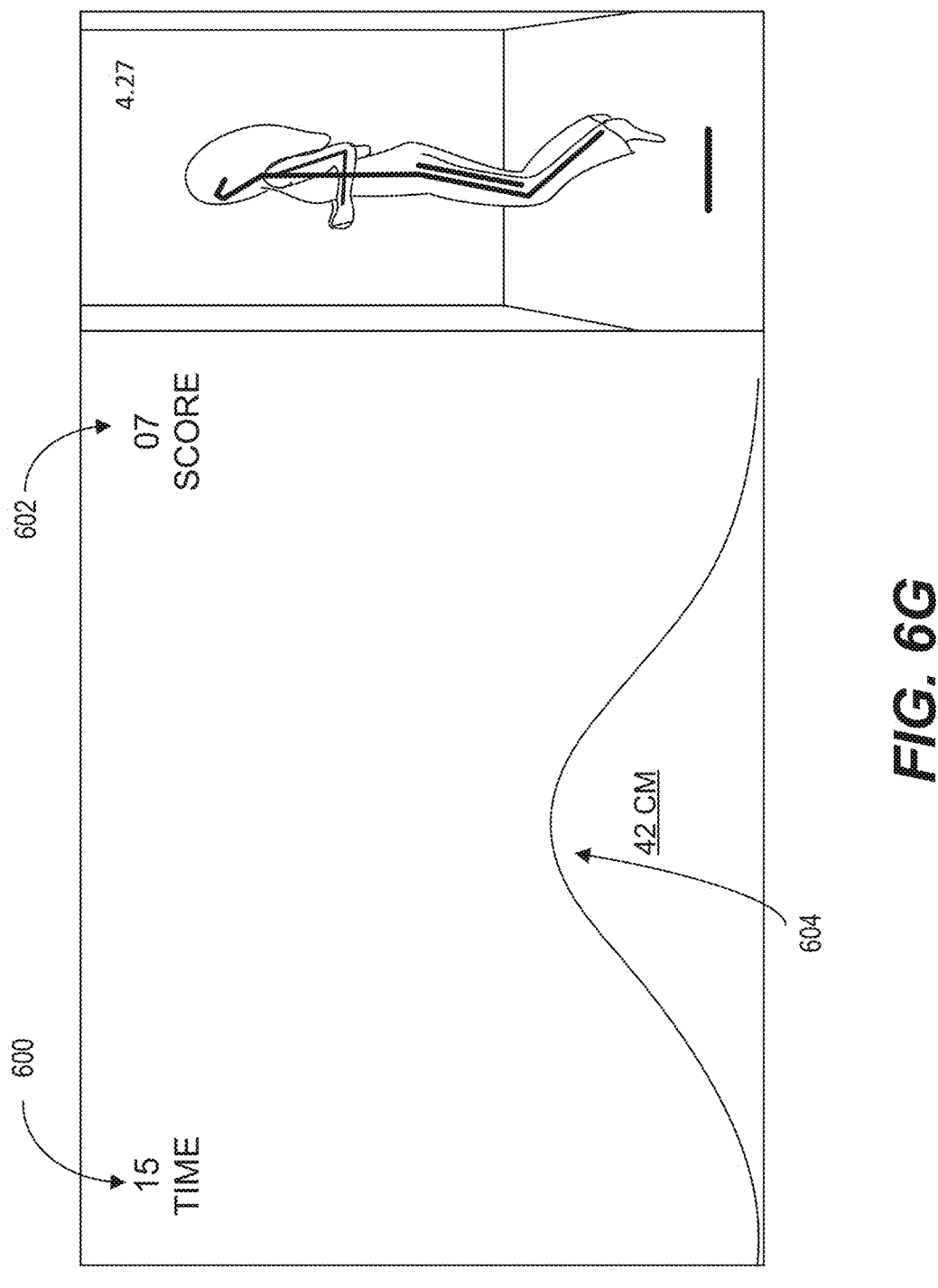
Figure 6H:
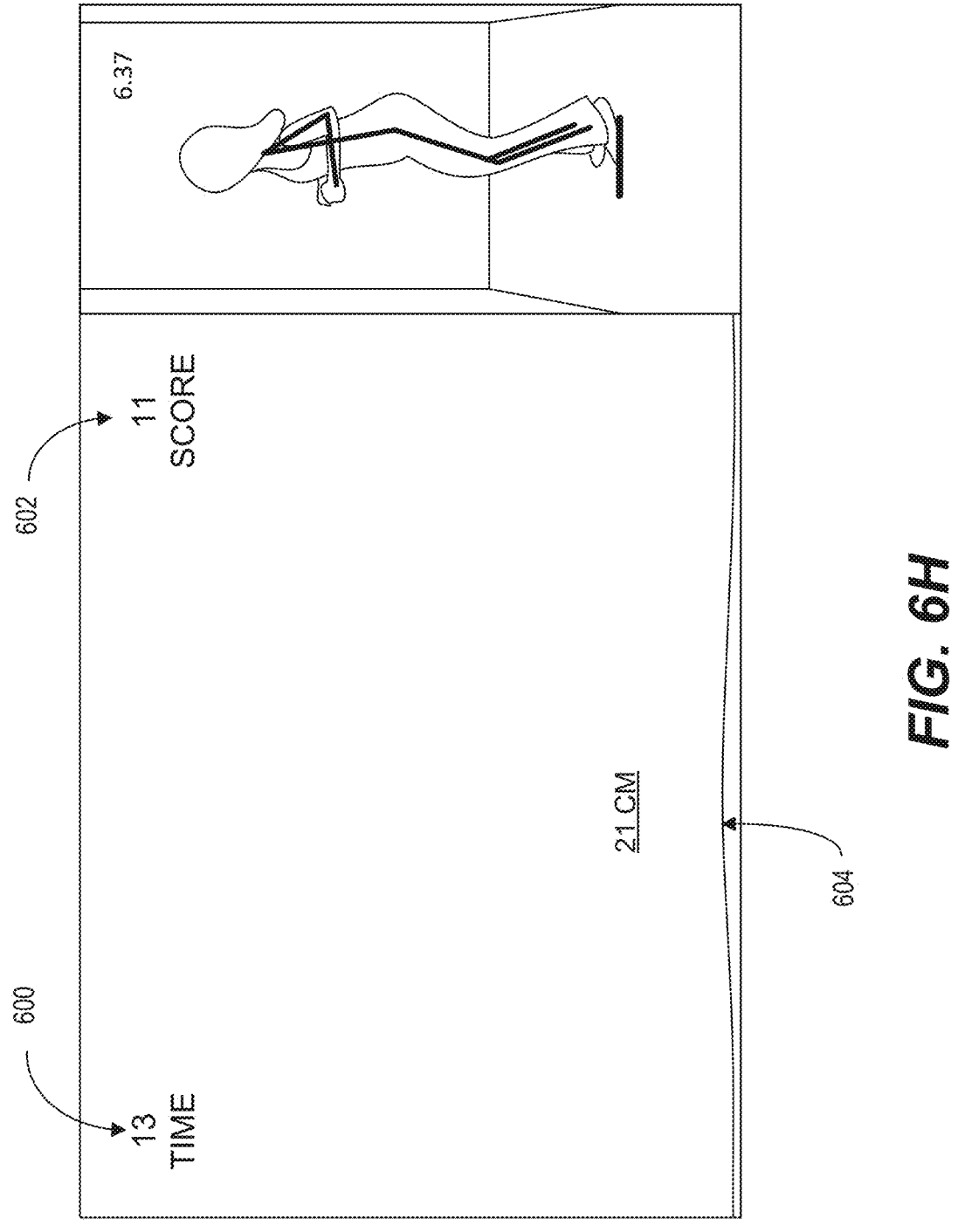
Figure 6I:
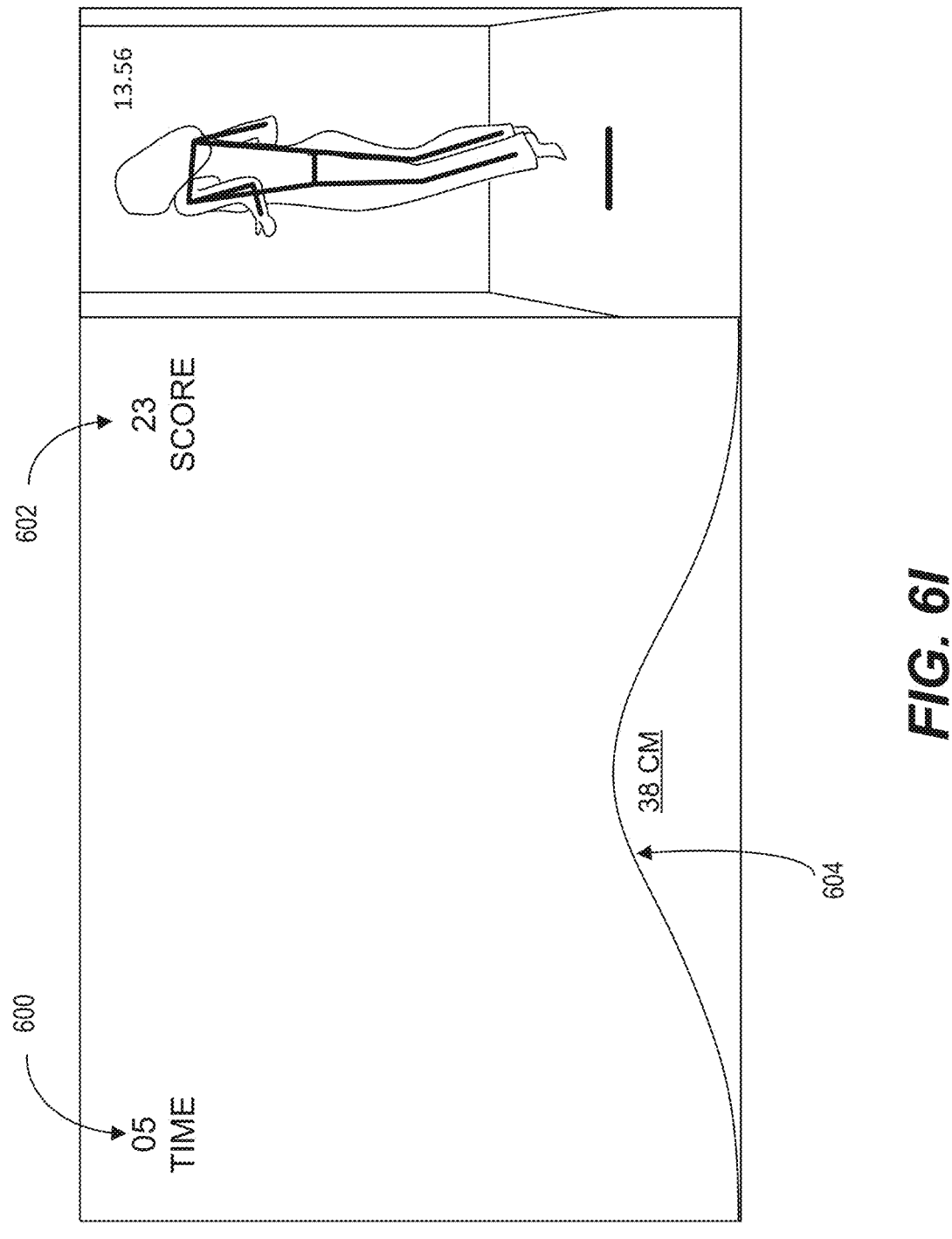

FIG. 6E illustrates a jumper 600 positioning herself to begin the jumping challenge upon receiving a prompt (e.g., "Jump!". The jumper may begin by entering the field of view of the camera (e.g., camera 175 of FIG. 8), allowing the CV engine to detect her. The time and score may be initialized to 0. A CV engine (e.g., CV engine 115) may determine a skeletal map for the jumper from multiple key points to track the distance of jumper from the surface during the jumping challenge. FIG. 6E illustrates FIG. 6F-6I illustrate the performance of the jumper tracked via the CV engine throughout the competition. The tracked performance may be displayed to the jumper in real-time, e.g., as feedback via output display device 306 of FIG. 3B. For example, time remaining 600, a cumulative jumping score 602, and the current height 604 may be displayed to the jumper, e.g., determined as the peak of a curve tracking the key points of the jumper).

Figure 6J:
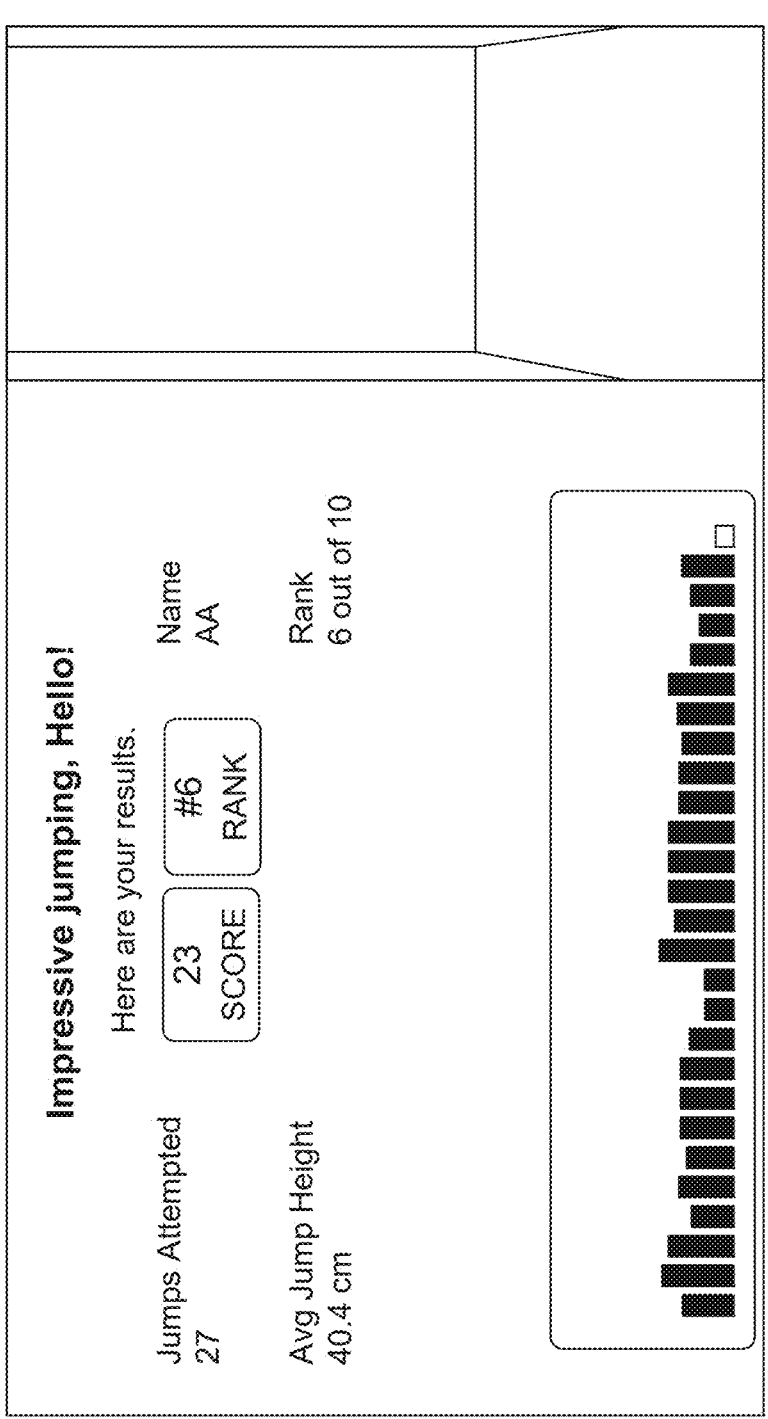

FIG. 6J illustrates an exemplary performance of the jumper during the competition. For example, the jumper's performance may be displayed via output display device 306 of FIG. 3B.

Figure 6L:
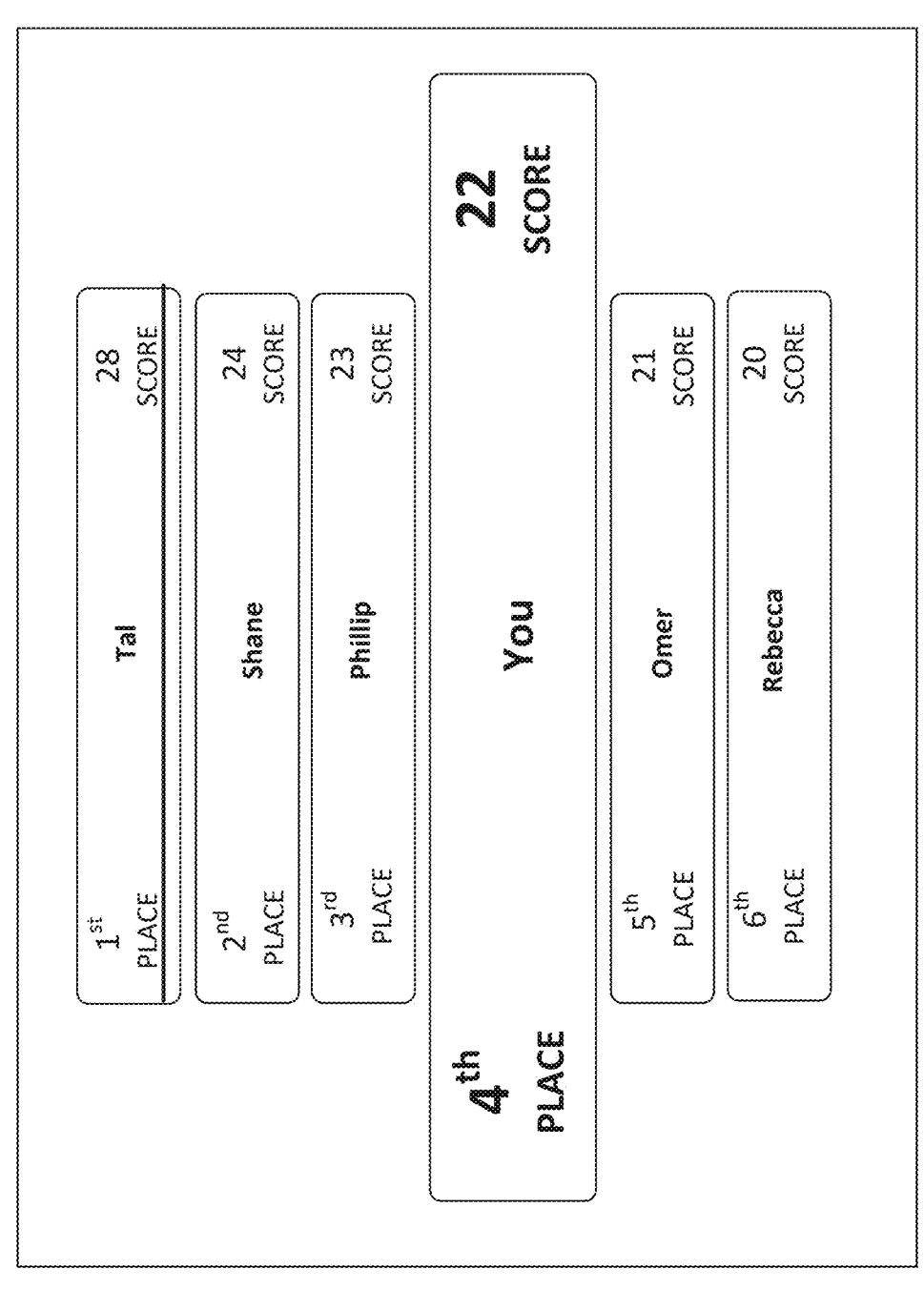

FIG. 6K illustrates an exemplary scoreboard comparing the jumper to other jumpers who participated in the jumping challenge, consistent with some disclosed embodiments. For example, the scoreboard may be displayed via leaderboard 308 of FIG. 3B. FIG. 6L illustrates another exemplary scoreboard comparing the jumper to other jumpers, consistent with some disclosed embodiments.

In some embodiments, feedback may be displayed to the jumper during the jumping challenge, for example to inform the jumper one or more of when the jumping challenge begins, how much time remains at each point during the challenge, how many jumps were performed, which jumps are determined to be qualifying jumps (e.g., and are therefore counted for the competition), the ratio of jumps that are qualifying jumps, and other jumpers currently competing in the jumping challenge. In some embodiments, the feedback may include an image or a live video of the jumper jumping in real time. In some embodiments, the feedback may include a moving graph following the motion of the jumper. The moving graph may indicate a qualifying threshold, allowing to compare the current motion of the jumper against the qualifying threshold.

In some embodiments, the leaderboard may display any of the location of the jumping challenge, the total number of qualifying jumps performed, the average jump height, the cumulative jump height, the maximum jump height, and a list of each jumper who competed in the jumping challenge with corresponding identifying data (e.g., name, image of the jumper) and a score indicating quantitative and/or qualitative performance of each jumper.

FIG. 7 illustrates a block diagram of an exemplary method for a CV engine facilitating a jumping competition, consistent with some disclosed embodiments.

In Step S702, the 3d point cloud data may be used to estimate the surface plane.

In Step S704, when the timer starts, a pose estimation algorithm may be executed to detect key points on the body of the jumper from a 2D image.

In Step S706, for each key point, the 3D location from the 3D camera may be sampled and the point to plane distance may be calculated between the 3D location and the surface plane.

In Step S708, the minimum of all the measured distances may be taken as the current body distance from the surface and the minimum may be stored with the timestamp information.

In Step S710, on the curve mapping the distance between the body and the surface over time, search for peaks. A peak may be a jump if it meets one or more criterion, such as there is no higher peak within a predetermined time period (e.g., too close), the peak to base delta is higher than a threshold, and any other qualifying criterion.

In Step S712, the peaks may be tallied as the number of jumps performed by the jumper.

FIG. 8 illustrates an exemplary implementation of a computer vision (CV) jump competition system 103 for facilitating a jumping challenge, consistent with some embodiments. The term "computer vision", (e.g., "CV") may refer to technology that enables computing devices to gain a high-level of understanding from digital visual media (e.g., images, video, and optionally accompanying metadata). CV may incorporate techniques from artificial intelligence (AI), deep learning, and image processing to derive meaningful information from digital visual media. For example, CV may allow a computing device to interpret an image to determine the context and make a recommendation based on the context.

In some embodiments, CV jump competition system 103 may include at least one computing device 105, a camera 175, and a database 195 communicatively coupled via a communications network 185. Computing device 105 may include a CV engine 115, a memory device 125, at least one processor 135, an input interface 155, an output interface 145, and a transceiver 165 communicatively coupled via a bus system 167. In some embodiments, CV jump competition system 103 may include a single computing device 105 providing both input and output interfaces. It is to be noted that a jumping challenge may be implemented on a training device so that the element of CV jump competition system 103 constitute a part of such a training device.

The term "CV engine" may refer to a package of hardware and/or software components for implementing CV. In some embodiments, a CV engine may detect and follow an object (e.g., a jumper) during a jumping challenge. For example, the CV engine may track both legs of the jumper as they push the jumper off a surface (e.g., a floor), determine which jumps are qualifying jumps, tally the total number of jumps (e.g., both qualifying and non-qualifying jumps), determine any of the average, maximum, and cumulative jump height for each jumper.

CV engine 115 may be implemented as one or more software libraries or applications executable by a processor, such as at least one processor 135. In some embodiments, CV engine 115 may include one or more dedicated processors. CV engine 115 may perform any combination of image processing, inference, machine learning, deep learning, artificial intelligence techniques on images acquired by camera 175.

Clauses Relating to an Exemplary Jumping Challenge:

Clause 1. A method for using a computer vision engine to determine a jumping score for a jumping challenge, the method comprising:

estimating a plane of a jumping surface;

using computer vision to identify a plurality of key points on a body of a jumper preparing to jump on a jumping surface;

over a time duration for the jumping challenge, capturing a plurality of images of the jumper jumping on the jumping surface;

for each of the plurality of images captured, use the computer vision engine to analyze the captured image and determine a distance between each key point on the body of the jumper and the jumping surface;

determine the minimum distance of the determined distances;

store the minimum distance with a time stamp corresponding to the moment the image was captured;

using the computer vision engine to identify at least one jump performed by the jumper based on tracking a plurality of minimum distances for a time series of the captured images;

adding the at least one identified jump to a jump tally for the jumper;

determining a jump height for each identified jump based on the maximum of the minimum distances identified with each identified jump;

when the determined jump height exceeds a predefined threshold, adding the at least one jump to a qualifying jump tally for the jumper;

storing the jump tally, the qualifying jump tally, and each determined jump height; and determining a score for the jumper based on one or more of the jump tally, the qualifying jump tally, and each determined jump height.

Clause 2. The method of clause 1, wherein the jumping surface is a floor.

Clause 3. The method of clause 1, wherein the plurality of key points are based on an image of the jumper Clause 4. The method of clause 1, wherein the score is further based on one or more of: a cumulative height jumped by the jumper, the cumulative height being a sum of each determined jumps height, a form of the jumper while jumping, a frequency of jumps performed by the jumper, a maximum of the determined jump heights, and a speed of a jump.

Systems and methods disclosed herein involve unconventional improvements over conventional approaches. Descriptions of the disclosed embodiments are not exhaustive and are not limited to the precise forms or embodiments disclosed. Modifications and adaptations of the embodiments will be apparent from consideration of the specification and practice of the disclosed embodiments. Additionally, the disclosed embodiments are not limited to the examples discussed herein.

The foregoing description has been presented for purposes of illustration. It is not exhaustive and is not limited to the precise forms or embodiments disclosed. Modifications and adaptations of the embodiments will be apparent from consideration of the specification and practice of the disclosed embodiments. For example, the described implementations include hardware and software, but systems and methods consistent with the present disclosure may be implemented as hardware alone.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and, accordingly, all suitable modifications and equivalents may be resorted to, falling within the scope of the disclosure.

Computer programs based on the written description and methods of this specification are within the skill of a software developer. The various functions, scripts, programs, or modules may be created using a variety of programming techniques. For example, programs, scripts, functions, program sections or program modules may be designed in or by means of languages, including JAVASCRIPT, C, C++, JAVA, PHP, PYTHON, RUBY, PERL, BASH, or other programming or scripting languages. One or more of such software sections or modules may be integrated into a computer system, non-transitory computer readable media, or existing communications software. The programs, modules, or code may also be implemented or replicated as firmware or circuit logic.

Moreover, while illustrative embodiments have been described herein, the scope may include any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. Further, the steps of the disclosed methods may be modified in any manner, including by reordering steps or inserting or deleting steps. It is intended, therefore, that the specification and examples be considered as exemplary only, with a true scope and spirit being indicated by the following claims and their full scope of equivalents.

What is claimed is:

1. A non-transitory computer readable medium containing instructions that when executed by at least one processor cause the at least one processor to perform asynchronous user-initiated and cloud mediated exertion challenge operations, comprising:

capturing via at least a first sensor first sensor data reflecting a first subject performing a first exertion, the first sensor data reflecting at least one parameter associated with the first exertion;

receiving an input to convert the first sensor data into a challenge;

receiving a selection of a second subject for receipt of the challenge;

causing transmission of the challenge to the second subject;

receiving from the second subject an electronic acceptance of the challenge;

capturing via a second sensor second sensor data reflecting the second subject performing a second exertion;

confirming via electronic comparison of the first sensor data and the second sensor data that the second exertion complies with the at least one parameter;

when the electronic comparison confirms that the second exertion complies with the at least one parameter of the first exertion, comparing metrics of the first sensor data and the second sensor data to determine a challenge dominator; and outputting a report to the first subject and the second subject identifying the challenge dominator.

2. The non-transitory computer readable medium of claim 1, wherein the least one parameter associated with the first exertion includes a particular type and a particular form of the first exertion.

3. The non-transitory computer readable medium of claim 2, wherein the particular exertion type includes an exercise category, and the particular exertion form includes a posture.

4. The non-transitory computer readable medium of claim 2, wherein the particular exertion type includes an exercise category, and the particular exertion form includes a minimum level of exertion.

5. The non-transitory computer readable medium of claim 1, wherein an electronic acceptance of the challenge includes the second sensor data reflecting the second subject performing the second exertion.

6. The non-transitory computer readable medium of claim 1, wherein the first exertion includes a series of exertion repetitions.

7. The non-transitory computer readable medium of claim 1, wherein the first sensor data and the second sensor data include outputs of resistive motors.

8. The non-transitory computer readable medium of claim 7, wherein each of the first sensor data and the second sensor data further include an output of an associated image sensors.

9. The non-transitory computer readable medium of claim 1, wherein the operations further comprise notifying the second subject of a time-period for receipt of the second sensor data and terminating the challenge when the second sensor data is not received during the time-period.

10. The non-transitory computer readable medium of claim 9, wherein the time-period extends hours from a time of receipt of the first data.

11. The non-transitory computer readable medium of claim 9, wherein prior to expiration of the time-period, the operations further comprise notifying the second subject that the first subject is dominant, and enabling the second subject to make at least one additional challenge attempt.

12. The non-transitory computer readable medium of claim 9, wherein the outputted report includes a leader board configured for dynamic information display during the time-period.

13. The non-transitory computer readable medium of claim 1, wherein receiving a selection of a second subject for receipt of the challenge includes receiving a selection of a class of subjects, and the second subject is part of the class.

14. The non-transitory computer readable medium of claim 13, wherein the class is defined by at least one of a geographical location, a friends group, or an age group.

15. The non-transitory computer readable medium of claim 1, wherein the outputted report includes a leader board.

16. The non-transitory computer readable medium of claim 1, wherein the operations further comprise receiving a selection of additional subjects for receipt of the challenge and causing transmission of the challenge to the additional subjects.

17. The non-transitory computer readable medium of claim 1, wherein the first sensor data and second sensor data correspond to motions of a cable, and include at least two of cable length pulled, cable velocity, a time interval between cable pulls, and an overall duration of a second set of exertions.

18. The non-transitory computer readable medium of claim 1, wherein comparing the metrics and outputting the report occurs on a server remote from the first subject and the second subject.

19. The non-transitory computer readable medium of claim 1, wherein the operations further comprise controlling a level of electrical current flowing through at least one resistive motor.

20. The non-transitory computer readable medium of claim 1, wherein at least one of the first exertion or the second exertion is performed on an electronic wall-mountable exercise machine.

21. The non-transitory computer readable medium of claim 1, wherein the first sensor data includes a first depth image and the second sensor data includes a second depth image.

22. A system for performing asynchronous user-initiated and cloud mediated exertion challenge operations, the system comprising:

at least one processor configured to:

capture via at least a first sensor first sensor data reflecting a first subject performing a first exertion, the first sensor data reflecting at least one parameter associated with the first exertion;

receive an input to convert the first sensor data into a challenge;

receive a selection of a second subject for receipt of the challenge;

cause transmission of the challenge to the second subject;

receive from the second subject an electronic acceptance of the challenge;

capture via a second sensor second sensor data reflecting the second subject performing a second exertion;

confirm via electronic comparison of the first sensor data and the second sensor data that that the second exertion complies with the at least one parameter;

when the electronic comparison confirms that the second exertion complies with the at least one parameter of the first exertion, compare metrics of the first sensor data and the second sensor data to determine a challenge dominator; and output a report to the first subject and the second subject identifying the challenge dominator.

23. A method for performing asynchronous user-initiated and cloud mediated exertion challenge operations, the method comprising:

capturing via at least a first sensor first sensor data reflecting a first subject performing a first exertion, the first sensor data reflecting at least one parameter associated with the first exertion;

receiving an input to convert the first sensor data into a challenge;

receiving a selection of a second subject for receipt of the challenge;

causing transmission of the challenge to the second subject;

receiving from the second subject an electronic acceptance of the challenge;

capturing via a second sensor second sensor data reflecting the second subject performing a second exertion;

confirming via electronic comparison of the first sensor data and the second sensor data that that the second exertion complies with the at least one parameter;

when the electronic comparison confirms that the second exertion complies with the at least one parameter of the first exertion, comparing metrics of the first sensor data and the second sensor data to determine a challenge dominator; and outputting a report to the first subject and the second subject identifying the challenge dominator.

\* \* \* \* \*